(12) United States Patent
Bourke, Jr.

(10) Patent No.: US 9,278,331 B2
(45) Date of Patent: *Mar. 8, 2016

(54) SYSTEMS AND METHODS FOR INTERIOR ENERGY-ACTIVATION FROM AN EXTERIOR SOURCE

(71) Applicant: IMMUNOLIGHT, LLC., Detroit, MI (US)

(72) Inventor: Frederic A. Bourke, Jr., Greenwich, CT (US)

(73) Assignee: IMMUNOLIGHT, LLC, Detroit, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/635,677

(22) Filed: Mar. 2, 2015

(65) Prior Publication Data

US 2015/0182934 A1 Jul. 2, 2015

Related U.S. Application Data

(63) Continuation of application No. 14/157,039, filed on Jan. 16, 2014, now Pat. No. 9,005,406, which is a continuation of application No. 13/713,974, filed on Dec. 13, 2012, now Pat. No. 8,658,086, which is a continuation of application No. 12/401,478, filed on Mar. 10, 2009, now Pat. No. 8,376,013.

(60) Provisional application No. 61/080,140, filed on Jul. 11, 2008, provisional application No. 61/035,559, filed on Mar. 11, 2008.

(51) Int. Cl.
*B01J 19/12* (2006.01)

(52) U.S. Cl.
CPC ................ *B01J 19/125* (2013.01); *B01J 19/12* (2013.01); *B01J 2219/1203* (2013.01)

(58) Field of Classification Search
CPC ........ B01J 19/12; B01J 19/122; B01J 19/123; B01J 19/125; B01J 2219/12; B01J 2219/1203
See application file for complete search history.

(56) References Cited

U.S. PATENT DOCUMENTS

| | | | |
|---|---|---|---|
| 2,721,941 A | 10/1955 | McMaster et al. | |
| 4,111,890 A | 9/1978 | Getson et al. | |
| 4,482,778 A | 11/1984 | Anderson | |
| 4,675,346 A | 6/1987 | Lin et al. | |
| 5,118,422 A | 6/1992 | Cooper et al. | |
| 5,323,442 A | 6/1994 | Golovanivsky et al. | |
| 5,829,448 A | 11/1998 | Fisher et al. | |
| 6,051,625 A | 4/2000 | Harkness et al. | |
| 6,087,141 A | 7/2000 | Margolis-Nunno et al. | |
| 6,281,261 B1 | 8/2001 | Bennington | |
| 6,323,253 B1 | 11/2001 | Bennington | |
| 6,344,272 B1 | 2/2002 | Oldenburg et al. | |
| 6,627,923 B1 | 9/2003 | Lipson et al. | |
| 6,750,266 B2 | 6/2004 | Bentsen et al. | |
| 7,005,229 B2 | 2/2006 | Nirmal et al. | |
| 7,008,559 B2 | 3/2006 | Chen | |
| 7,014,988 B2 | 3/2006 | DeVoe et al. | |
| 7,091,255 B2 | 8/2006 | DeVoe | |
| 7,208,890 B2 | 4/2007 | Zavadtsev et al. | |
| 7,265,161 B2 | 9/2007 | Leatherdale et al. | |
| 7,267,948 B2 | 9/2007 | Vo-Dinh | |
| 7,294,656 B2 | 11/2007 | Bach et al. | |
| 7,297,374 B1 | 11/2007 | Arney et al. | |
| 7,381,516 B2 | 6/2008 | Arney et al. | |
| 7,601,484 B2 | 10/2009 | DeVoe et al. | |
| 7,790,347 B2 | 9/2010 | Leatherdale et al. | |
| 8,236,239 B2 | 8/2012 | Bernstein | |
| 8,376,013 B2 * | 2/2013 | Bourke, Jr. et al. | 156/379.6 |
| 8,927,615 B2 * | 1/2015 | Bourke, Jr. et al. | 522/4 |
| 9,004,131 B2 | 4/2015 | Bourke, Jr. et al. | |
| 2002/0045675 A1 | 4/2002 | Halas et al. | |
| 2002/0103517 A1 | 8/2002 | West et al. | |
| 2002/0119485 A1 | 8/2002 | Morgan | |
| 2002/0161065 A1 | 10/2002 | DiTizio et al. | |
| 2003/0139484 A1 | 7/2003 | Bentsen et al. | |
| 2003/0219785 A1 | 11/2003 | Hallahan et al. | |
| 2004/0067431 A1 | 4/2004 | Arney et al. | |
| 2004/0198857 A1 | 10/2004 | Dejneka et al. | |
| 2004/0253138 A1 | 12/2004 | Malak | |
| 2005/0020869 A1 | 1/2005 | Hainfeld et al. | |
| 2005/0031077 A1 | 2/2005 | Avnery | |
| 2005/0276382 A1 | 12/2005 | Lesiak et al. | |
| 2006/0011862 A1 | 1/2006 | Bernstein | |
| 2007/0018140 A1 | 1/2007 | Lee et al. | |
| 2007/0063154 A1 | 3/2007 | Chen et al. | |
| 2007/0153283 A1 | 7/2007 | Tsao et al. | |
| 2007/0178133 A1 | 8/2007 | Rolland | |
| 2007/0217996 A1 | 9/2007 | Levy et al. | |
| 2007/0218049 A1 | 9/2007 | Chen et al. | |
| 2007/0257232 A1 | 11/2007 | Tai et al. | |

(Continued)

FOREIGN PATENT DOCUMENTS

| | | |
|---|---|---|
| CN | 1270186 A | 10/2000 |
| CN | 1463286 A | 12/2003 |

(Continued)

OTHER PUBLICATIONS

K. Jensen, J. Weldon, H. Garcia, and A. Zettl, "Nanotube Radio," *Nano Lett.*, vol. 7, No. 11, 3508-3511 (2007).

(Continued)

*Primary Examiner* — Sanza McClendon
(74) *Attorney, Agent, or Firm* — Oblon, McClelland, Maier & Neustadt, L.L.P

(57) ABSTRACT

A method and a system for producing a change in a medium. The method places in a vicinity of the medium at least one energy modulation agent. The method applies an initiation energy to the medium. The initiation energy interacts with the energy modulation agent to directly or indirectly produce the change in the medium. The system includes an initiation energy source configured to apply an initiation energy to the medium to activate the energy modulation agent.

41 Claims, 5 Drawing Sheets

(56) References Cited

U.S. PATENT DOCUMENTS

| | | | |
|---|---|---|---|
| 2008/0004364 | A1 | 1/2008 | Huo et al. |
| 2008/0248001 | A1 | 10/2008 | Bourke |
| 2009/0130169 | A1 | 5/2009 | Bernstein |
| 2009/0263744 | A1 | 10/2009 | Kuroki |
| 2010/0261263 | A1 | 10/2010 | Vo-Dinh et al. |
| 2013/0156905 | A1 | 6/2013 | Bourke, Jr. et al. |
| 2014/0163303 | A1 | 6/2014 | Bourke, Jr. et al. |
| 2014/0222117 | A1 | 8/2014 | Bourke, Jr. et al. |

FOREIGN PATENT DOCUMENTS

| | | |
|---|---|---|
| CN | 101035827 A | 9/2007 |
| EP | 1 353 179 A1 | 10/2003 |
| EP | 1355193 | 10/2003 |
| EP | 1 870 478 A1 | 12/2007 |
| EP | 2 265 366 | 12/2010 |
| EP | 2 711 075 A2 | 3/2014 |
| JP | 58-183940 | 10/1983 |
| JP | 59-4436 | 1/1984 |
| JP | 60-186575 A | 9/1985 |
| JP | 8-217982 A | 8/1996 |
| JP | 10-11822 A | 1/1998 |
| JP | A H10-11822 | 1/1998 |
| JP | 2001-46488 A | 2/2001 |
| JP | 2001-334262 | 12/2001 |
| JP | 2002-214142 | 7/2002 |
| JP | 2003-313208 | 11/2003 |
| JP | 2005-138440 A | 6/2005 |
| JP | 2006-298908 A | 11/2006 |
| JP | 2006-323908 A | 11/2006 |
| JP | 2007-104939 | 4/2007 |
| JP | 2007-156184 A | 6/2007 |
| JP | 2007-171158 | 7/2007 |
| JP | 2013-82943 A | 5/2013 |
| WO | WO 01/47438 A1 | 7/2001 |
| WO | WO 2006/013944 A1 | 2/2006 |
| WO | WO 2007/072689 | 6/2007 |
| WO | WO 2009/114567 A1 | 9/2009 |

OTHER PUBLICATIONS

Douglas D. Young and Alexander Deiters, "Photochemical Hammerhead Ribozyme Activation", *Bioorganic & Medicinal Chemistry Letters*, 16(10) ,pp. 2658-2661 (2006).
Hirsch, L. R., Stafford, R.J., Bankson, J.A., Sershen, S.R., Rivera, B., Price, R.E., Hazle, J. D., Halas, N. J., and West, J. L., *Nanoshell-mediated near-infrared thermal therapy of tumors under magnetic resonance guidance*. PNAS, 2003. 100(23): p. 13549-13554.
Xiaohua Huang & Prashant K. Jain & Ivan H. El-Sayed & Mostafa A. El-Sayed, Plasmonic photothermal therapy (PPTT) using gold nanoparticles, *Lasers in Medical Science*, Aug. 2007.
Mircea Cotlet, Tom Vosch, Satoshi Habuchi, Tanja Weil, Klaus Mullen, Johan Hofkens, and Frans De Schryver, "*Probing Intramolecular Forster Resonance Energy Transfer in a Naphthaleneimide- Peryleneimide-Terrylenediimide-Based Dendrimer by Ensemble and ingle-Molecule Fluorescence Spectroscopy*", J. Am. Chem. Soc. 2005, 127, 9760-9768.
M.O. Guler, "Singlet-Singlet and Triplet-Triplet Energy Transfer in Bichromophoric Cyclic Peptides," Worcester Polytechnic Institute, May 18, 2002.
Young and Deiters in "Photochemical Control of Biological Processes", *Org. Biomol. Chem.*, 5, pp. 999-1005 (2007).
T. Vo-Dinh, M.Y.K. Hiromoto, G. M. Begun and R. L. Moody, "Surface-enhanced Raman spectroscopy for trace organic analysis," *Anal. Chem.*, vol. 56, 1667, 1984.
M. M. Kerker, Electromagnetic Model for Surface-Enhanced Raman Scattering (SERS) on Metal Colloids, *Acc. Chem. Res.*, 17, 370 (1984).
T. Vo-Dinh, "Surface-Enhanced Raman Spectroscopy Using Metallic Nanostructures," *Trends in Anal. Chem.*, 17,557 (1998).
J. B. Jackson, S. L. Westcott, L. R. Hirsch, J. L. West and N. H. Halas, "Controlling the surface enhanced Raman effect via the nanoshell geometry," *Appl. Phys. Lett.*, vol. 82, 257-259, 2003.
S. J. Norton and T. Vo-Dinh, "Plasmonic Resonances of nanoshells of Spheroidal Shape", *IEEE Trans. Nanotechnology*, 6, 627-638 (2007).
R. Elghanian, J.J. Storhoff, R.C. Mucic, R.L. Letsinger and C.A. Mirkin, Selective colorimetric detection of polynucleotides based on the distance-dependent optical properties of gold nanoparticles. *Science* 277 (1997), pp. 1078-1081.
Z. Li, R.C. Jin, C.A. Mirkin and R.L. Letsinger, Multiple thiol-anchor capped DNA-gold nanoparticle conjugates. *Nucleic Acids Res.* 30 (2002), pp. 1558-1562.
Y.W. Cao, R. Jin and C.A. Mirkin, DNA-modified core-shell Ag/Au nanoparticles. *J. Am. Chem. Soc.* 123 (2001), pp. 7961-7962.
Burgess, J. D.; Hawkridge, F. M., "*Octadecyl Mercaptan Submonolayers on Silver Electrodeposited on Gold Quartz Crystal Microbalance Electrodes*", Langmuir 1997, 13, 3781-6.
Hainfeld et al, Gold nanoparticles: a new X-ray contrast agent, *The British Journal of radiology*, 79, 248, 2006.
Ma et al, DNA-Passivated CdS Nanocrystals : Luminescence, Bioimaging, and Toxicity Profiles, *Langmuir*, 23 (26), 12783-12787 (2007).
Hua et al, Soft x-ray excited optical luminescence : Some recent applications, *Rev. Sci. Instrum.* ,, 73, 1379. 2002.
Jaegle et al, Ultraviolet luminescence of CsI and CsCl excited by soft x-ray laser, *J. Appl. Phys.*, 81, 2406, 1997.
Kun Chen, Yang Liu, Guillermo Ameer, Vadim Backman, Optimal design of structured nanospheres for ultrasharp light-scattering resonances as molecular imaging multilabels, *Journal of Biomedical Optics*, 10(2), 024005 (Mar./Apr. 2005).
Mirkhin et al, X-ray excited luminescence of some molybdates, *Nuclear Instrum. Meth. In Physics Res. A*, 486, 295 (2002).
L. Soderholm, G. K. Liu, Mark R. Antoniol, F. W. Lytle, X-ray excited optical luminescence .XEOL. detection of x-ray absorption fine structure .XAFZ, *J. Chem. Phys*,109, 6745, 1998.
Masashi Ishiia, Yoshihito Tanaka and Tetsuya Ishikawa, Shuji Komuro and Takitaro Morikawa, Yoshinobu Aoyagi, Site-selective x-ray absorption fine structure analysis of an optically active center in Er-doped semiconductor thin film using x-ray-excited optical luminescence, *Appl. Phys. Lett*, 78, 183, Jan. 8, 2001.
Kuiru Li, Mark I. Stockman, and David J. Bergman, Self-Similar Chain of Metal Nanospheres as an Efficient Nanolens, *Physical Review Letter*, vol. 91, No. 22, 227402-1, 2003.
Frens, G., *Controlled nucleation for the regulation of the particle size in monodisperse gold solutions*. Nature (London) Phys Sci 1973. 241: p. 20-22.
Lei Zhang, Joe Swift, Christopher A. Butts, Vijay Yerubandi and Ivan J. Dmochowski, Structure and activity of apoferritin-stabilized gold nanoparticles, Journal of Inorganic Biochemistry, vol. 101, 1719-1729, 2007.
Keiko Yoshizawa, Kenji Iwahori, Kenji Sugimoto and Ichiro Yamashita, Fabrication of Gold Sulfide Nanoparticles Using the Protein Cage of Apoferritin, Chemistry Letters, vol. 35 (2006), No. 10 p. 1192.
Martin Nikl, Scintillation detectors for x-rays, *Meas. Sci. Technol.* 17 (2006) R37-R54.
Kadshchuk, A. K., Ostapenko, N. I., Skryshevskii, Yu. A., Sugakov, V. I. and Susokolova, T. O., *Clusters of Dipole Charge-Carrier Capture Centers in Organic Crystals, Mol. Cryst. and Liq. Cryst.*, 201, 167 (1991).
S. V. Izvekov, V. I. Sugakov, Exciton and Electron Traps on Structural Defects in Molecular Crystals with Dipolar Molecules, *Physica Scripta*. vol. T66, 255-257, 1996.
A. P. D'Silva, G. J. Oestreich, and V. A. Fassel, X-ray excited optical luminescence of polynuclear aromatic hydrocarbons, *Anal. Chem.*; 1976; 48(6) pp. 915-917.
T. Vo-Dinh, Multicomponent analysis by synchronous luminescence spectrometry, *Anal. Chem.*; 1978; 50(3) pp. 396-401.
J. Bellessa, C. Bonnand, and J. C. Plenet, J. Mugnier, Strong Coupling between Surface Plasmon and Excitons in an Organic Semiconductor, *Phys. Rev. Lett*, 93 (3), 036404-1, 2004.
Alexander O. Govorov, Garnett W. Bryant,‡ Wei Zhang, Timur Skeini, Jaebeom Lee,§ Nicholas A. Kotov, Joseph M. Slocik,| and Rajesh R. Naik, Exciton-Plasmon Interaction and Hybrid Excitons in Semiconductor-Metal Nanoparticle Assemblies, *Nano Lett.*, vol. 6, No. 5, 984, 2006.

(56) References Cited

OTHER PUBLICATIONS

I.V. Bondarev, K. Tatur and L.M. Woods, *Strong exciton-plasmon coupling in semiconducting carbon nanotube*, Jul. 8, 2009 Accepted paper in Physical Review B.
Yuri Fedutik, Vasily Temnov, Ulrike Woggon, Elena Ustinovich, and Mikhail Artemyev, Exciton-Plasmon Interaction in a Composite Metal-Insulator-Semiconductor Nanowire System, *J. . Am. Chem. Soc.*, 129 (48), 14939 -14945, 2007.
G.W. Ford and W. H. Weber, Electromagnetic interactions of molecules with metal surfaces, *Phys. Rep.* 113, 195-287 (1984).
Gregory A. Wurtz, Paul R. Evans, William Hendren, Ronald Atkinson, Wayne Dickson, Robert J. Pollard, and Anatoly V. Zayats, Molecular Plasmonics with Tunable Exciton-Plasmon Coupling Strength in J-Aggregate Hybridized Au Nanorod Assemblies, *Nano Lett.*, vol. 7, No. 5, 1297, 2007.
Jaebeom Lee, Alexander O. Govorov, John Dulka, and Nicholas A. Kotov, Bioconjugates of CdTe Nanowires and Au Nanoparticles: Plasmon-Exciton Interactions, Luminescence Enhancement, and Collective Effects, *Nano Lett.*, vol. 4, No. 12, 2323, 2004.
N.R. Jana, L. Gearheart and C.J. Murphy, Seeding growth for size control of 5-40 nm diameter gold nanoparticles. *Langmuir* 17 (2001), pp. 6782-6786.
Brust, M.; Walker, M.; Bethell, D.; Schiffrin, D. J.; Whyman, R., *Synthesis of Thiol-derivatised Gold Nanoparticles in a Two-phase Liquid-Liquid System Chem. Commun.* 1994, 801.
Hostetler, M.J.; Wingate, J. E.; Zhong, C. J.; Harris, J. E.; Vachet, R. W.; Clark, M. R.; Londono, J. D.; Green, S. J.; Stokes, J. J.; Wignall, G. D.; Glish, G. L.; Porter, M. D.; Evans, N. D.; Murray, R. W., Alkanethiolate Gold Cluster Molecules with Core Diameters from 1.5 to 5.2 nm: Core and Monolayer Properties as a Function of Core Size, *Langmuir* 1998, 14, 17.
Schmid, G.; Pfeil, R.; Boese, R.; Bandrmann, F.; Meyer, S.; Calis, G. H. M.; van der Velden, J. W. A., $Au55[P(C_6H_5)_3]_{12}Cl_6$—*ein Goldcluster ungewohnlicher Größe, Chem. Ber.* 1981, 114, 3634; with English Abstract.
Warner, M. G.; Reed, S. M.; Hutchison, J. E., Small, Water-Soluble, Ligand-Stabilized Gold Nanoparticles Synthesized by Interfacial Ligand Exchange Reactions, *Chem. Mater.* 2000,12, 3316.
Weare, W. W.; Reed, S. M.; Warner, M. G.; Hutchison, J. E., Improved Synthesis of Small ($d_{CORE}$ ≈1.5 nm) Phosphine-Stabilized Gold Nanoparticles, *J. Am. Chem. Soc.* 2000, 122, 12890.
Ziyi Zhong, Benoit Male, Keith B. Luong, John H.T., *More Recent Progress in the Preparation of Au Nanostructures, Properties, and Applications, Analytical Letters*; 2003, vol. 36 Issue 15, p. 3097-3118.
Akito Masuhara, Satoshi Ohhashi, Hitoshi Kasai; Shuji Okada, Fabrication and Optical Properties of Nanocomplexes Composed of Metal Nanoparticles and Organic Dyes, *Journal of Nonlinear Optical Physics & Materials* vol. 13, Nos. 3 & 4 (2004) 587-592.
Wang et al. in "Electromagnetic excitation of nano-carbon in vacuum," in Optics Express, vol. 13, No. 10, May 10, 2005.
Aslan et al. in "Multicolor Microwave-Triggered Metal-Enhanced Chemiluminescence," in J. Am. Chem. Soc. published on Web Sep. 23, 2006.
M. A. Correa-Duarte, M. Giesig, and L. M. Liz-Marzan, *Stabilization of CdS semiconductor nanoparticles against photodegradation by a silica coating procedure*, Chem. Phys. Lett., 1998, 286: 497.
M. Thomas, H. von Seggern, *Method for the determination of phostostimulable defect center concentrations, production rates, and effective formation energies*, J. Appl. Phys. 1994, 75: 4658-4661.
W. Chen, S. P. Wang, S. Westcott, J. Zhang, A. G. Joly, and D. E. McCready, *Structure and luminescence of $BaFBr:Eu^{2+}$ and $BaFBR:Eu^{2+}, Tb^{3+}$ phosphors and thin films*, J. Appl. Phys. 2005, 97: 083506.
Mai Thu Thi Tran, Mohammed Farid, "Ultraviolet Treatment of Orange Juice" published in Innoveative Food Science & Emerging Technologies (vol. 5, Issue 4, Dec. 2004, pp. 495-502).
Santos et al, *Photocatalysis as a Tertiary Treatment for Petroleum Refinery Wastewaters*, Braz. J. Chem. Eng. vol. 23, No. 4, 2006.

Spatio-Resolved Hyperbranched Graft Polymerized Surfaces by Iniferter-Based Photograft Copolymerization, *Langmuir*, 2002, 18 (7), pp. 2601-2606.
Pettinger B., U. Wenneng, and H. Wetzel, Surface-plasmon enhanced Raman-scattering Frequency and Angular Resonance of Raman Scattered Light From Pyridine on Au, Ag and Cu Electrodes, 1980, Surf. Sci., 101, 409.
Fleishman M., P. R. Graves, and J. Robinson, *The Raman-Spectroscopy of the Ferricyanide/Ferrocyanide System at Gold, β-Palladium Hydride and Platinum Electrodes*, 1985, J. Electroanal. Chem., 182, 87.
Miller S. K., A. Baiker, M. Meier, and A. Wokaun, *Surface-enhanced Raman scattering and the preparation of copper substrates for catalytic studies*, 1984, J. Chem. Soc. Farad. Trans. I, 80, 1305.
Taranenko N., J.P. Alarie, D.L. Stokes, and T. Vo Dinh, *Surface-Enhanced Raman Detection of Nerve Agent Simulant (DMMP and DIMP) Vapor on Electrochemically Prepared Silver Oxide Substrates*, 1996, J. Raman Spectr., 27, 379-384.
Jennings C., R. Aroca, A. M. Hor, and R. O. Loutfy, *Surface-enhanced Raman scattering from copper and zinc phthalocyanine complexes by silver and indium island films*, 1984, Anal. Chem., 56, 203.
Ni F., R. Sheng, and T. M. Cotton, *Flow-injection analysis and real-time Detection of RNA bases by surface-enhanced Raman-spectroscopy*, 1990, Anal. Chem., 62, 1958.
Moody R. L., T. Vo Dinh, and W. H. Fletcher, *Investigation of Experimental Parameters for Surface-Enhanced Raman Scattering (SERS) Using Silver-Coated Microsphere Substrates*, 1987, Appl. Spectr., 41, 966.
Bello J. M., D. L. Stokes and T. Vo Dinh, *Silver-Coated Alumina as a New Medium for Surface-Enhanced Raman Scattering Analysis*, 1989, Appl. Spectrosc., 43. 1325.
Sutherland, *A Portable Surface-Enhanced Raman Spectrometer*, Instrumentation Science & Technology, vol. 22, Issue 3 Aug. 1994, pp. 231-239.
Alak A., and T. Vo Dinh, *Silver-Coated Fumed Silica as New Substrate Materials for Surface-Enhanced Raman Scattering*, 1989, Anal. Chem., 61, 656.
Liao P. F., and M. B. Stern, *Surface-enhanced Raman scattering on gold and aluminum particle arrays*, 1982, Opt. Lett., 7, 483.
Vo Dinh T., M. Meier, and A. Wokaun, 1986, *Surface Enhanced Raman Spectroscopy with Silver Particles on Stochastic Post Substrates*, Anal. Chim. Acta, 181, 139.
Enlow P. D., M. C. Buncick, R. J. Warmack, and T. Vo Dinh, *Detection of Nitro polynuclear Aromatic Compounds by Surface Enhanced Raman Spectroscopy*, 1986, Anal. Chem., 58, 1119.
Vo Dinh T., 1989, *Surface-Enhanced Raman Spectrometry, in Chemical Analysis of Polycyclic Aromatic Compounds*, Wiley, T. Vo-Dinh, Ed., New York.
M. Volkan, D.L. Stokes and T. Vo-Dinh, *A Sol-Gel Derived AgCl Photochromic Coating on Glass for SERS Chemical Sensor Application*, Sensors and Actuators B, 106, 660-667 (2004).
Search Report issued Mar. 20, 2013 in Chilean Patent Application No. 2009-000560 filed Mar. 10, 2009 (with English Translation of Categories of Cited Documents).
Japanese Office Action Issued Feb. 26, 2013 in Patent Application No. 2013-015222 (with English translation).
Combined Chinese Office Action and Search Report Issued Jan. 30, 2013 in Patent Application No. 200980116914.1 (English translation only).
M. Venkataraman, "Effects of Cryopreservation on Immune Responses" Cryobiology 34, Article No. CY972005, 1997, pp. 276-283.
Douglas D. Young, et al. "Photochemical control of biological processes" Organic & Biomolecular Chemistry,vol. 5, Dec. 20, 2006, pp. 999-1005.
Kadir Aslan, et al. "Multicolor Microwave-Triggered Metal-Enhanced Chemiluminescence"JACS Communications, Journal of the American Chemical Society,Sep. 2006, pp. 13372-13373.
Shaomin Wang, et al. "Electromagnetic excitation of nano-carbon in vacuum" Optics Express, vol. 13, No. 10, May 16, 2005, pp. 3625-3630.

(56) References Cited

OTHER PUBLICATIONS

Rahul M. Rasal, et al. "Effect of the Photoreaction Solvent on Surface and Bulk Properties of Poly(lactic acid) and Poly(hydroxyalkanoate) Films" Journal of Biomedical Material Research Part B: Applied Biometerials, 2007, pp. 564-572.

Combined Office Action and Search Report issued Mar. 17, 2014 in Chinese Patent Application No. 201310057456.7 (w/English translation).

Notice of Reasons for Rejection issued Jul. 31, 2012 in Japanese Patent Application No. 2010-550826 (with English translation).

Steffi Artz et al., Automation of Macromolecular Crystallography Beamlines, Progress in Biophysics and Molecular Biology, Oct. 2005, vol. 89, Issue 2, pp. 124-152.

Combined Office Action and Search Report issued on Dec. 26, 2013 in Taiwan Patent Application No. 098107921.

Decision of Rejection issued Sep. 8, 2014 in Japanese Patent Application No. 2010-550826 (w/English translation).

Decision to Reject the Amendments issued Sep. 8, 2014 in Japanese Patent Application No. 2010-550826 (w/English translation).

Office Action issued Jun. 18, 2014 in Chinese Patent Application No. 200980116914.1 (w/English translation).

Notice of Reasons for Rejection issued Mar. 31, 2014 in Japanese Patent Application No. 2013-015222 (w/English translation).

Office Action issued Oct. 16, 2013 in Chilean Patent Application No. 2009-000560 (w/English translation of Categories of Cited Documents).

Combined Chinese Office Action and Search Report issued Nov. 27, 2013 in Chinese Patent Application No. 200980116914.1 (w/English translation).

Decision of Rejection issued Sep. 3, 2013 in Japanese Patent Application No. 2013-015222 (with English translation).

Office Action issued on Jul. 2, 2013 in the corresponding Japanese Patent Application No. 2010-550826 (with English Translation).

Extended Search Report issued Mar. 16, 2015 in European Patent Application No. 13 189 150.9.

Office Action issued Feb. 9, 2015 in Japanese Application No. 2013-272032 (with English language translation).

Japanese Office Action issued on Nov. 20, 2015 in corresponding Japanese Patent Application No. 2013-272032.

\* cited by examiner

| ENDOGENOUS FLUOROPHORES | EXCITATION MAX. (nm) | EMISSION MAX. (nm) |
|---|---|---|
| Amino acids: | | |
| Tryptophan | 280 | 350 |
| Tyrosine | 275 | 300 |
| Phenylalanine | 260 | 280 |
| Structured Proteins: | | |
| Collagen | 325,360 | 400 |
| Elastin | 290,325 | 405 |
| Enzymes and Coenzymes: | | |
| flavine adenine dinucleatide | 450 | 535 |
| reduced nicotinamidedinucleotide | 290,351 | 440,460 |
| reduced nicotinamide dinucleotide phosphate | 336 | 464 |
| Vitamins: | | |
| Vitamin A | 327 | 510 |
| Vitamin K | 335 | 480 |
| Vitamin D | 390 | 480 |
| Vitamins $B_2$ compounds: | | |
| Pyridoxine | 332,340 | 400 |
| Pyridoxamine | 335 | 400 |
| Pyridoxal | 330 | 385 |
| Pyridoxic acid | 315 | 425 |
| Pyridoxal phosphate | 5'-330 | 400 |
| Vitamin $B_{12}$ | 275 | 305 |
| Lipids: | | |
| Phospholipids | 436 | 540,560 |
| Lipofuscin | 340-395 | 540,430-460 |
| Ceroid | 340-395 | 430-460,540 |
| Porphyrins | 400-450 | 630,690 |

*Fig.2*

SYSTEMS AND METHODS FOR INTERIOR ENERGY-ACTIVATION FROM AN EXTERIOR SOURCE

CROSS REFERENCE TO RELATED APPLICATIONS

This application is a continuation of U.S. Ser. No. 14/157,039 filed Jan. 16, 2014. U.S. Ser. No. 14/157,039 is a continuation of U.S. Ser. No. 13/713,974 filed Dec. 13, 2012 which is a continuation of Ser. No. 12/401,478 filed Mar. 10, 2009, the entire contents of each are incorporated herein by reference. This application is related to provisional Ser. No. 60/910,663, filed Apr. 8, 2007, entitled "METHOD OF TREATING CELL PROLIFERATION DISORDERS," and non-provisional Ser. No. 11/935,655, filed Nov. 6, 2007, entitled "METHOD OF TREATING CELL PROLIFERATION DISORDERS," the contents of each of which are hereby incorporated herein by reference. This application is related to provisional Ser. No. 61/035,559, filed Mar. 11, 2008, entitled "SYSTEMS AND METHODS FOR INTERIOR ENERGY-ACTIVATION FROM AN EXTERIOR SOURCE," the entire contents of which are hereby incorporated herein by reference.

THE NAMES OF THE PARTIES TO A JOINT RESEARCH AGREEMENT

Immunolight, LLC and Duke University are parties to a joint research agreement in place at the time of the invention.

BACKGROUND OF THE INVENTION

1. Field of Invention

The invention relates to methods and systems for generating in the interior of a medium or body radiant energy for producing a change in the properties of a medium or body by exposure to the radiation.

2. Discussion of the Background

Presently, light (i.e., electromagnetic radiation from the radio frequency through the visible to the x-ray and gamma ray wavelength range) activated processing is used in a number of industrial processes ranging from photoresist curing, to on-demand ozone production, to sterilization, to the promotion of polymer cross-linking activation (e.g. in adhesive and surface coatings) and others. Today, light activated processing is seen in these areas to have distinct advantages over more conventional approaches. For example, conventional sterilization by steam autoclaving or in food processing by pasteurization may unsuitably overheat the medium to be sterilized. As such, light activated curable coatings are one of the fastest growing sectors in the coatings industry. In recent years, this technology has made inroads into a number of market segments like fiber optics, optical and pressure-sensitive adhesives, and automotive applications like cured topcoats, and curable powder coatings. The driving force of this development is mostly the quest for an increase in productivity of the coating and curing process, as conventional non light activated adhesive and surface coatings typically require 1) the elimination of solvents from the adhesive and surface coatings to produce a cure and 2) a time/temperature cure which adds delay and costs to the manufacturing process.

Moreover, the use of solvent based products in adhesive and surface coatings applications is becoming increasingly unattractive because of rising energy costs and stringent regulation of solvent emissions into the atmosphere. Optimum energy savings as well as beneficial ecological considerations are both served by radiation curable adhesive and surface coating compositions. Radiation curable polymer cross-linking systems have been developed to eliminate the need for high oven temperatures and to eliminate the need for expensive solvent recovery systems. In those systems, light irradiation initiates free-radical cross-linking in the presence of common photo sensitizers.

However, in the adhesive and surface coating applications and in many of the other applications listed above, the light-activated processing is limited due to the penetration depth of light into the processed medium. For example, in water sterilization, ultraviolet light sources are coupled with agitation and stirring mechanisms in order to ensure that any bacteria in the water medium will be exposed to the UV light. In light-activated adhesive and surface coating processing, the primary limitation is that the material to be cured must be directly exposed to the light, both in type (wavelength or spectral distribution) and intensity. In adhesive and surface coating applications, any "shaded" area will require a secondary cure mechanism, increasing cure time over the non-shaded areas and further delaying cure time due to the existent of a sealed skin through which subsequent curing must proceed (i.e., referred to as a cocoon effect).

SUMMARY OF THE INVENTION

The invention overcomes the problems and disadvantages of the prior art as described in the various embodiments below.

In one embodiment, there is provided a method and system for producing a change in a medium disposed in an artificial container. The method (1) places in a vicinity of the medium an energy modulation agent, and (2) applies an initiation energy from an applied initiation energy source through the artificial container to the medium. The applied initiation energy interacts with the energy modulation agent to directly or indirectly produce the change in the medium. The system includes the artificial container configured to contain the medium including the energy modulation agent. The system further includes an applied initiation energy source configured to apply the initiation energy through the artificial container to the medium to activate the energy modulation agent.

In another embodiment, there is provided a method and system for curing a radiation-curable medium. The method applies an applied energy throughout a composition including an uncured radiation-curable medium and an energy modulation agent. The applied initiation energy interacts with the energy modulation agent to directly or indirectly cure the medium by polymerization of polymers in the medium. The system includes an initiation energy source configured to apply initiation energy to the composition.

It is to be understood that both the foregoing general description of the invention and the following detailed description are exemplary, but are not restrictive of the invention.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein:

FIG. 2 is a table providing a list of photoactivatable agents;

DETAILED DESCRIPTION OF THE INVENTION

Figure 1:
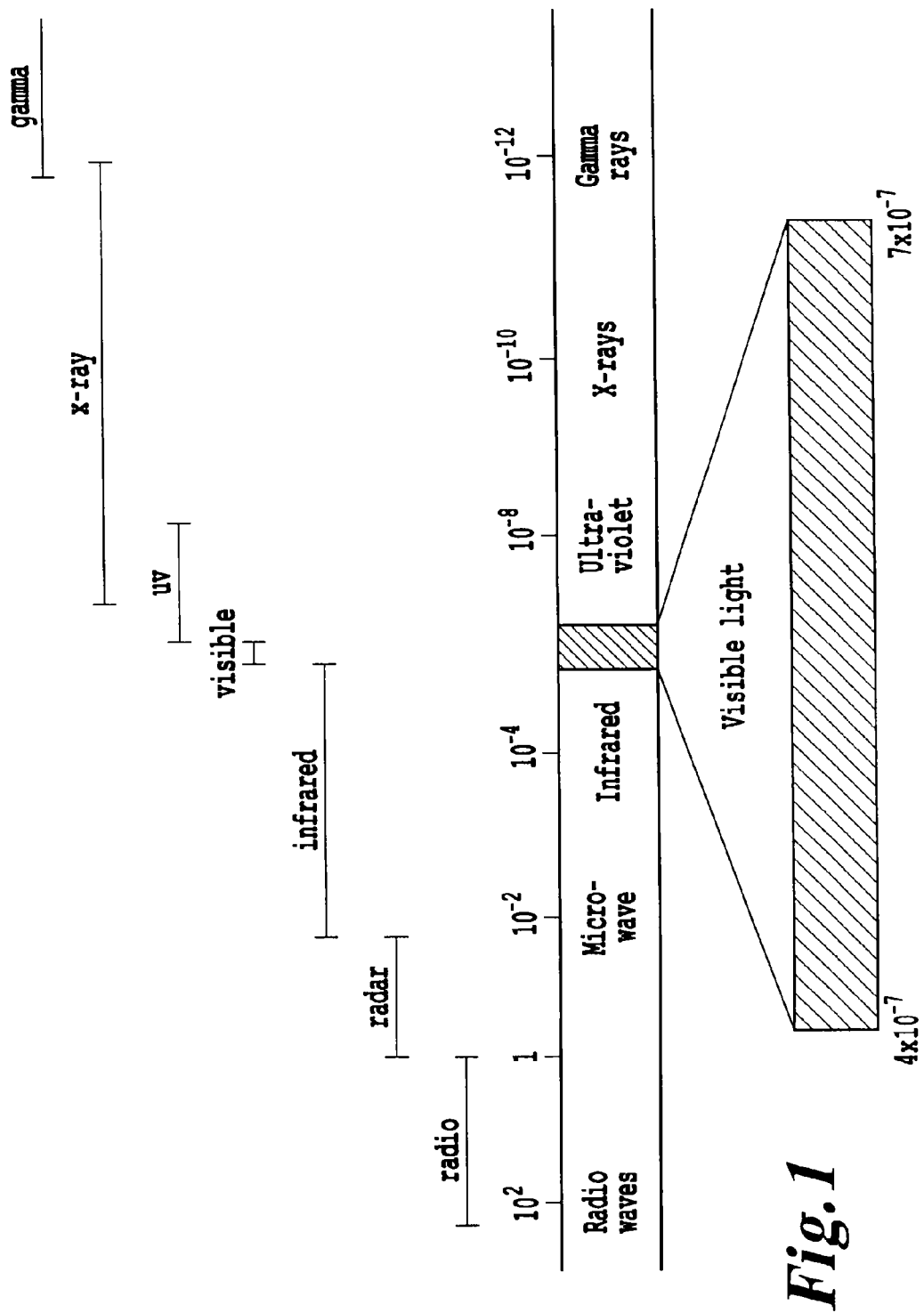
FIG. 1 provides an exemplary electromagnetic spectrum in meters (1 nm equals $10^{-9}$ meters)

The invention sets forth a novel method for causing a change in activity of an in a medium that is effective, specific, and able to produce a change to the medium.

Generally, the invention provides methods for producing a change in a medium after generation of radiant light inside the medium. In this method, an initiation energy source provides an initiation energy that penetrates the medium and induces internal radiation to produce a desired effect in the medium.

In one embodiment, the initiation energy source is applied directly or indirectly to the medium. Within the context of the invention, the phrase "applied indirectly" (or variants of this phrase, such as "applying indirectly", "indirectly applies", "indirectly applied", "indirectly applying", etc.), when referring to the application of the initiation energy, means the penetration by the initiation energy into the medium beneath the surface of the medium and to the activatable agent or energy modulation agents within a medium. In one embodiment, the initiation energy interacts with a previously supplied energy modulation agent which then activates the activatable agent.

Although not intending to be bound by any particular theory or be otherwise limited in any way, the following theoretical discussion of scientific principles and definitions are provided to help the reader gain an understanding and appreciation of the invention.

As used herein, an "activatable agent" is an agent that normally exists in an inactive state in the absence of an activation signal. When the agent is activated by an activation signal under activating conditions, the agent is capable of producing a desired pharmacological, cellular, chemical, electrical, or mechanical effect in a medium (i.e. a predetermined change). For example, when photocatalytic agents are irradiated with visible or UV light, these agents induce polymerization and "curing" of light sensitive adhesives.

Signals that may be used to activate a corresponding agent may include, but are not limited to, photons of specific wavelengths (e.g. x-rays, or visible light), electromagnetic energy (e.g. radio or microwave), thermal energy, acoustic energy, or any combination thereof. Activation of the agent may be as simple as delivering the signal to the agent or may further require a set of activation conditions. For example, an activatable agent, such as a photosensitizer, may be activated by UV-A radiation (e.g., by UV-A radiation generated internally in the medium). Once activated, the agent in its active-state may then directly proceed to produce a predetermined change.

Where activation may further require other conditions, mere delivery of the activation signal may not be sufficient to bring about the predetermined change. For example, a photoactive compound that achieves its effect by binding to certain structure in its active state may require physical proximity to the target structure when the activation signal is delivered. For such activatable agents, delivery of the activation signal under non-activating conditions will not result in the desired effect. Some examples of activating conditions may include, but are not limited to, temperature, pH, location, state of the medium, and the presence or absence of co-factors.

Selection of an activatable agent greatly depends on a number of factors such as the desired change, the desired form of activation, as well as the physical and biochemical constraints that may apply. Exemplary activatable agents may include, but are not limited to agents that may be activated by photonic energy, electromagnetic energy, acoustic energy, chemical or enzymatic reactions, thermal energy, microwave energy, or any other suitable activation mechanisms.

When activated, the activatable agent may effect changes that include, but are not limited to an increase in organism activity, a fermentation, a decrease in organism activity, apoptosis, redirection of metabolic pathways, a sterilization of a medium, a cross polymerization and curing of a medium, or a cold pasteurization of a medium.

The mechanisms by which an activatable agent may achieve its desired effect are not particularly limited. Such mechanisms may include direct action on a predetermined target as well as indirect actions via alterations to the biochemical pathways. In one embodiment, the activatable agent is capable of chemically binding to the organism in a medium. In this embodiment, the activatable agent, is exposed in situ to an activating energy emitted from an energy modulation agent, which, in turn receives energy from an initiation energy source.

Suitable activatable agents include, but are not limited to, photoactive agents, sono-active agents, thermo-active agents, and radio/microwave-active agents. An activatable agent may be a small molecule; a biological molecule such as a protein, a nucleic acid or lipid; a supramolecular assembly; a nanoparticle; or any other molecular entity capable of producing a predetermined activity once activated.

The activatable agent may be derived from a natural or synthetic origin. Any such molecular entity that may be activated by a suitable activation signal source to effect a predetermined cellular change may be advantageously employed in the invention.

Suitable photoactive agents include, but are not limited to: psoralens and psoralen derivatives, pyrene cholesteryloleate, acridine, porphyrin, fluorescein, rhodamine, 16-diazorcortisone, ethidium, transition metal complexes of bleomycin, transition metal complexes of deglycobleomycin, organoplatinum complexes, alloxazines such as 7,8-dimethyl-10-ribityl isoalloxazine (riboflavin), 7,8,10-trimethylisoalloxazine (lumiflavin), 7,8-dimethylalloxazine (lumichrome), isoalloxazine-adenine dinucleotide (flavine adenine dinucleotide [FAD]), alloxazine mononucleotide (also known as flavine mononucleotide [FMN] and riboflavine-5-phosphate), vitamin Ks, vitamin L, their metabolites and precursors, and napththoquinones, naphthalenes, naphthols and their derivatives having planar molecular conformations, porphyrins, dyes such as neutral red, methylene blue, acridine, toluidines, flavine (acriflavine hydrochloride) and phenothiazine derivatives, coumarins, quinolones, quinones, and anthroquinones, aluminum (111) phthalocyanine tetrasulfonate, hematoporphyrin, and phthalocyanine, and compounds which preferentially adsorb to nucleic acids with little or no effect on proteins. The term "alloxazine" includes isoalloxazines.

Endogenously-based derivatives include synthetically derived analogs and homologs of endogenous photoactivated molecules, which may have or lack lower (1 to 5 carbons) alkyl or halogen substitutes of the photosensitizers from which they are derived, and which preserve the function and substantial non-toxicity. Endogenous molecules are inherently non-toxic and may not yield toxic photoproducts after photoradiation.

FIG. 1 provides an exemplary electromagnetic spectrum in meters (1 nm equals 1 nanometer). As used herein, an "energy modulation agent" refers to an agent that is capable of receiving an energy input from a source and then re-emitting a different energy to a receiving target. Energy transfer among molecules may occur in a number of ways. The form of energy may be electronic, thermal, electromagnetic, kinetic, or chemical in nature. Energy may be transferred from one molecule to another (intermolecular transfer) or from one part of a molecule to another part of the same molecule (intramolecular transfer). For example, a modulation agent may receive electromagnetic energy and re-emit the energy in the form of thermal energy.

Table 1 in FIG. 2 provides a list of photoactivatable agents that may be used as primary or secondary internal light sources. For example, the photoactivatable agents could be receptors of X-ray induced emissions from nanoparticles (to be discussed later) and which in turn emit a secondary light. In some mediums, it may be that the excitation wavelengths in Table 1 are transparent to the particular medium and the emission wavelengths are highly absorbent (due to, for example, molecular or solid state band gap transitions). In those cases, the photoreactive agents in Table 1 would be the primary sources for internal light generation.

In various embodiments, the energy modulation agent receives higher energy (e.g. x-ray) and re-emits in lower energy (e.g. UV-A). Some modulation agents may have a very short energy retention time (on the order of fs, e.g. fluorescent molecules) whereas others may have a very long half-life (on the order of minutes to hours, e.g. luminescent or phosphorescent molecules). Suitable energy modulation agents include, but are not limited to, a biocompatible fluorescing metal nanoparticle, fluorescing dye molecule, gold nanoparticle, a water soluble quantum dot encapsulated by polyamidoamine dendrimers, a luciferase, a biocompatible phosphorescent molecule, a combined electromagnetic energy harvester molecule, and a lanthanide chelate capable of intense luminescence. Typically, the energy modulation agents induce photoreactive changes in the medium and are not used for the purpose of exclusively heating the medium.

Various exemplary uses are described in the embodiments below.

The modulation agents may further be coupled to a carrier for targeting purposes. For example, a biocompatible molecule, such as a fluorescing metal nanoparticle or fluorescing dye molecule that emits in the UV-A band, may be selected as the energy modulation agent. The energy modulation agent may be preferably directed to the desired site by systemic administration into a medium. For example, a UV-A emitting energy modulation agent may be distributed in the medium by physical insertion and or mixing, or by conjugating the UV-A emitting energy modulation agent with a specific carrier, such as a lipid, chitin or chitin-derivative, a chelate or other functionalized carrier that is capable of concentrating the UV-A emitting source in a specific target region of the medium.

Additionally, the energy modulation agent can be used alone or as a series of two or more energy modulation agents such that the energy modulation agents provide an energy cascade. Thus, the first energy modulation agent in the cascade will absorb the activation energy, convert it to a different energy which is then absorbed by the second energy modulation in the cascade, and so forth until the end of the cascade is reached with the final energy modulation agent in the cascade emitting the energy necessary to activate the activatable agent. Alternatively, one or more energy modulation agents in the cascade may also activate additional activatable agents.

Although the activatable agent and the energy modulation agent can be distinct and separate, it will be understood that the two agents need not be independent and separate entities. In fact, the two agents may be associated with each other via a number of different configurations. Where the two agents are independent and separately movable from each other, they can generally interact with each other via diffusion and chance encounters within a common surrounding medium. Where the activatable agent and the energy modulation agent are not separate, they may be combined into one single entity.

The initiation energy source can be any energy source capable of providing energy at a level sufficient to activate the activatable agent directly, or to provide the energy modulation agent with the input needed to emit the activation energy for the activatable agent (indirect activation). Preferable initiation energy sources include, but are not limited to, ultraviolet lamps such as UV-A and UV-B lamps, halogen lamps, fiber optic lines, a light needle, an endoscope, self-ballasted mercury vapor lamps, ballasted HID lamps, and any device capable of generating x-ray, y-ray, gamma-ray, or electron beams.

In one embodiment, the initiation energy is capable of penetrating completely through the medium. Within the context of the invention, the phrase "capable of penetrating completely through the medium" is used to refer to energy capable of penetrating a container to any distance necessary to activate the activatable agent within the medium. It is not required that the energy applied actually pass completely through the medium, merely that it be capable of doing so in order to permit penetration to any desired distance to activate the activatable agent. The type of energy source chosen will depend on the medium itself. Exemplary initiation energy sources that are capable of penetrating completely through the medium include, but are not limited to, x-rays, gamma rays, electron beams, microwaves and radio waves.

In one embodiment, the source of the initiation energy can be a radiowave emitting nanotube, such as those described by K. Jensen, J. Weldon, H. Garcia, and A. Zettl in the Department of Physics at the University of California at Berkeley (see http://socrates.berkeley.edu/~argon/nanoradio/radio.html, the entire contents of which are hereby incorporated by reference). These nanotubes can be introduced to the medium, and preferably would be coupled to the activatable agent or the energy modulation agent, or both, such that upon application of the initiation energy, the nanotubes would accept the initiation energy (preferably radiowaves), then emit radiowaves in close proximity to the activatable agent, or in close proximity to the energy modulation agent, to then cause activation of the activatable agent. In such an embodiment, the nanotubes would act essentially as a radiowave focusing or amplification device in close proximity to the activatable agent or energy modulation agent.

Alternatively, the energy emitting source may be an energy modulation agent that emits energy in a form suitable for absorption by a transfer agent or for direct interaction with components of the medium. For example, the initiation energy source may be acoustic energy, and one energy modulation agent may be capable of receiving acoustic energy and emitting photonic energy (e.g. sonoluminescent molecules) to be received by another energy modulation agent that is capable of receiving photonic energy. Other examples include transfer agents that receive energy at x-ray wavelength and emit energy at UV wavelength, preferably at UV-A wavelength. As noted above, a plurality of such energy modulation agents may be used to form a cascade to transfer energy from initiation energy source via a series of energy modulation agents to activate the activatable agent.

Photoactivatable agents may be stimulated by an energy source through mechanisms such as irradiation, resonance energy transfer, exciton migration, electron injection, or chemical reaction, to an activated energy state that is capable of producing the predetermined change desired. One advantage is that wavelengths of emitted radiation may be used to selectively stimulate one or more photoactivatable agents or energy modulation agents capable of stimulating the one or more photoactivatable agents. The energy modulation agent is suitably stimulated at a wavelength and energy that causes little or no change to the medium.

In another embodiment, the photoactivatable agent is stimulated via a resonance energy transfer. Resonance Energy Transfer (RET) is an energy transfer mechanism between two molecules having overlapping emission and absorption bands. Electromagnetic emitters are capable of converting an arriving wavelength to a longer wavelength. For example, UV-B energy absorbed by a first molecule may be transferred by a dipole-dipole interaction to a UV-A-emitting molecule in close proximity to the UV-B-absorbing molecule. One advantage is that multiple wavelengths of emitted radiation may be used to selectively stimulate one or more photoactivatable agents or energy modulation agents capable of stimulating the one or more photoactivatable agents. With RET, the energy modulation agent is preferably stimulated at a wavelength and energy that causes little or no effect to the surrounding medium with the energy from one or more energy modulation agents being transferred, such as by Foerster Resonance Energy Transfer, to the photoactivatable agents.

Alternatively, a material absorbing a shorter wavelength may be chosen to provide RET to a non-emitting molecule that has an overlapping absorption band with the transferring molecule's emission band. Alternatively, phosphorescence, chemiluminescence, or bioluminescence may be used to transfer energy to a photoactivatable molecule.

Alternatively, one can apply the initiation energy source to the medium. Within the context of the invention, the applying of the initiation energy source means the application of an agent, that itself produces the initiation energy, in a manner that permits the agent to arrive at the target structure within the medium. In this embodiment, the initiation energy source includes, but is not limited to, chemical energy sources, nanoemitters, nanochips, and other nanomachines that produce and emit energy of a desired frequency.

Recent advances in nanotechnology have provided examples of various devices that are nanoscale and produce or emit energy, such as the Molecular Switch (or Mol-Switch) work by Dr. Keith Firman of the EC Research and Development Project, or the work of Cornell et al. (1997) who describe the construction of nanomachines based around ion-channel switches only 1.5 nm in size, which use ion channels formed in an artificial membrane by two gramicidin molecules: one in the lower layer of the membrane attached to a gold electrode and one in the upper layer tethered to biological receptors such as antibodies or nucleotides. When the receptor captures a target molecule or cell, the ion channel is broken, its conductivity drops, and the biochemical signal is converted into an electrical signal. These nanodevices could also be coupled with the invention to provide targeting of the target cell, to deliver the initiation energy source directly at the desired site.

In another embodiment, the invention includes the application of the activatable agent, along with a source of chemical energy such as chemiluminescence, phosphorescence or bioluminescence. The source of chemical energy can be a chemical reaction between two or more compounds, or can be induced by activating a chemiluminescent, phosphorescent or bioluminescent compound with an appropriate activation energy, either outside the medium or inside the medium, with the chemiluminescence, phosphorescence or bioluminescence being allowed to activate the activatable agent in the medium. The administration of the activatable agent and the source of chemical energy can be performed sequentially in any order or can be performed simultaneously.

In the case of certain sources of such chemical energy, the application of the chemical energy source can be performed after activation outside the medium, with the lifetime of the emission of the energy being up to several hours for certain types of phosphorescent materials for example.

Yet another example is that nanoparticles or nanoclusters of certain atoms may be introduced such that they are capable of resonance energy transfer over comparatively large distances, such as greater than one nanometer, more preferably greater than five nanometers, even more preferably at least 10 nanometers. Functionally, resonance energy transfer may have a large enough "Foerster" distance ($R_0$), such that nanoparticles in one part of a medium are capable of stimulating activation of photoactivatable agents disposed in a distant portion of the medium, so long as the distance does not greatly exceed $R_0$. For example, gold nanospheres having a size of 5 atoms of gold have been shown to have an emission band in the ultraviolet range, recently.

Any of the photoactivatable agents may be exposed to an excitation energy source provided in the medium. The photoactive agent may be directed to a receptor site by a carrier having a strong affinity for the receptor site. Within the context of the invention, a "strong affinity" is preferably an affinity having an equilibrium dissociation constant, $K_i$, at least in the nanomolar, nM, range or higher. The carrier may be a polypeptide and may form a covalent bond with a photoactive agent, for example. Alternatively, a photoactive agent may have a strong affinity for the target molecule in the medium without binding to a carrier.

In one embodiment, a plurality of sources for supplying electromagnetic radiation energy or energy transfer is provided by one or more molecules provided to the medium. The molecules may emit stimulating radiation in the correct band of wavelength to stimulate the photoactivatable agents, or the molecules may transfer energy by a resonance energy transfer or other mechanism directly to the photoactivatable agent or indirectly by a cascade effect via other molecular interactions.

In a further embodiment, a biocompatible emitting source, such as a fluorescing metal nanoparticle or fluorescing dye molecule, is selected that emits in the UV-A band. UV-A and the other UV bands are known to be effective as germicides.

In one embodiment, the UV-A emitting source is a gold nanoparticle comprising a cluster of 5 gold atoms, such as a water soluble quantum dot encapsulated by polyamidoamine dendrimers. The gold atom clusters may be produced through a slow reduction of gold salts (e.g. $HAuCl_4$ or $AuBr_3$) or other encapsulating amines, for example. One advantage of such a gold nanoparticle is the increased Foerster distance (i.e. $R_0$), which may be greater than 100 angstroms. The equation for determining the Foerster distance is substantially different from that for molecular fluorescence, which is limited to use at distances less than 100 angstroms. It is believed that the gold nanoparticles are governed by nanoparticle surface to dipole equations with a $1/R^4$ distance dependence rather than a $1/R^6$ distance dependence. For example, this permits cytoplasmic to nuclear energy transfer between metal nanoparticles and a photoactivatable molecule.

In another embodiment, a UV or light-emitting luciferase is selected as the emitting source for exciting a photoactivatable agent. A luciferase may be combined with molecules, which may then be oxygenated with additional molecules to stimulate light emission at a desired wavelength. Alternatively, a phosphorescent emitting source may be used. Phosphorescent materials may have longer relaxation times than fluorescent materials, because relaxation of a triplet state is subject to forbidden energy state transitions, storing the energy in the excited triplet state with only a limited number of quantum mechanical energy transfer processes available for returning to the lower energy state. Energy emission is delayed or prolonged from a fraction of a second to several hours. Otherwise, the energy emitted during phosphorescent relaxation is not otherwise different than fluorescence, and the range of wavelengths may be selected by choosing a particular phosphor.

In another embodiment, a combined electromagnetic energy harvester molecule is designed, such as the combined light harvester disclosed in J. Am. Chem. Soc. 2005, 127, 9760-9768, the entire contents of which are hereby incorporated by reference. By combining a group of fluorescent molecules in a molecular structure, a resonance energy transfer cascade may be used to harvest a wide band of electromagnetic radiation resulting in emission of a narrow band of fluorescent energy. By pairing a combined energy harvester with a photoactivatable molecule, a further energy resonance transfer excites the photoactivatable molecule, when the photoactivatable molecule is nearby stimulated combined energy harvester molecules. Another example of a harvester molecule is disclosed in FIG. 4 of "Singlet-Singlet and Triplet-Triplet Energy Transfer in Bichromophoric Cyclic Peptides," M. S. Thesis by M. O. Guler, Worcester Polytechnic Institute, May 18, 2002, which is incorporated herein by reference.

In another embodiment, a Stokes shift of an emitting source or a series of emitting sources arranged in a cascade is selected to convert a shorter wavelength energy, such as X-rays, to a longer wavelength fluorescence emission such a optical or UV-A, which is used to stimulate a photoactivatable molecule in the medium.

In an additional embodiment, the photoactivatable agent can be a photocaged complex having an active agent (which can be a cytotoxic agent if cytotoxicity is needed, or can be an activatable agent) contained within a photocage. In various embodiments, where the active agent is a cyotoxic agent, the photocage molecule releases the cytotoxic agent into the medium where it can attack non-beneficial "target" species in the medium. The active agent can be bulked up with other molecules that prevent it from binding to specific targets, thus masking its activity. When the photocage complex is photoactivated, the bulk falls off, exposing the active agent. In such a photocage complex, the photocage molecules can be photoactive (i.e. when photoactivated, they are caused to disso- ciate from the photocage complex, thus exposing the active agent within), or the active agent can be the photoactivatable agent (which when photoactivated causes the photocage to fall off), or both the photocage and the active agent are photoactivated, with the same or different wavelengths. Suitable photocages include those disclosed by Young and Deiters in "Photochemical Control of Biological Processes", *Org. Biomol. Chem.*, 5, pp. 999-1005 (2007) and "Photochemical Hammerhead Ribozyme Activation", *Bioorganic & Medicinal Chemistry Letters*, 16(10), pp. 2658-2661 (2006), the contents of which are hereby incorporated by reference.

Work has shown that the amount of singlet oxygen necessary to cause cell lysis, and thus cell death, is $0.32 \text{ H } 10^{-3}$ mol/liter or more, or $10^9$ singlet oxygen molecules/cell or more. In one embodiment of the invention, the level of singlet oxygen production caused by the initiation energy or the activatable agent upon activation is sufficient to cause a change in a medium, wherein the medium becomes free from any microorganisms. Microorganisms include but are not limited to bacteria, viruses, yeasts or fungi. To this end, singlet oxygen in sufficient amounts as described above can be used to sterilize the medium.

For example, medical bottle caps need to be sterilized between the base cap material and the glued seal material which contacts the base of the medical bottle. Because steam autoclaves are insufficient for this purpose, one embodiment of the invention uses UV luminescing particles included in the adhesive layer when the seal material is applied to the bottle cap. Then, X-ray irradiation becomes capable of curing the adhesive and producing within the adhesive medium UV radiation for direct sterilization or the production of singlet oxygen or ozone for biological germicide.

The activatable agent and derivatives thereof as well as the energy modulation agent, can be incorporated into compositions suitable for delivery to particular mediums. The composition can also include at least one additive having a complementary effect upon the medium, such as a lubricant or a sealant.

The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Figure 3A:
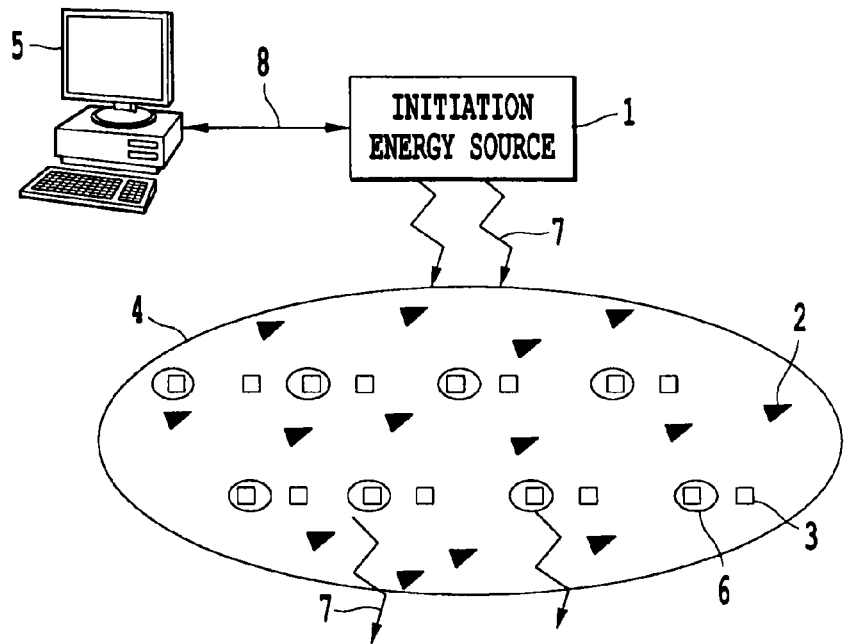
FIG. 3A is a schematic depicting a system according to one embodiment of the invention in which an initiation energy source is directed to a self-contained medium for producing changes in the medium.

Referring to FIG. 3A, an exemplary system according to one embodiment of the invention may have an initiation energy source 1 directed at medium 4. Activatable agents 2 and an energy modulation agents 3 are dispersed throughout the medium 4. The initiation energy source 1 may additionally be connected via a network 8 to a computer system 5 capable of directing the delivery of the initiation energy. In various embodiments, the energy modulation agents 3 are encapsulated energy modulation agents 6, depicted in FIG. 3A as silica encased energy modulation agents. As shown in FIG. 3A, initiation energy 7 in the form of radiation from the initiation energy source 1 permeated throughout the medium 4. A more thorough discussion of the computer system 5 is provided below in reference to FIG. 4. As discussed below in more detail, the initiation energy source 1 can be an external energy source or an energy source located at least partially in the medium 4.

In various embodiments, the initiation energy source 1 may be a linear accelerator equipped with image guided computer-control capability to deliver a precisely calibrated beam of radiation to a pre-selected coordinate. One example of such linear accelerators is the SmartBeam™ IMRT (intensity modulated radiation therapy) system from Varian medical systems (Varian Medical Systems, Inc., Palo Alto, Calif.). In other embodiments, the initiation energy source 1 may be commercially available components of X-ray machines or non-medical X-ray machines. X-ray machines that produce from 10 to 150 keV X-rays are readily available in the marketplace. For instance, the General Electric Definium series or the Siemens MULTIX series are but two examples of typical X-ray machines designed for the medical industry, while the Eagle Pack series from Smith Detection is an example of a non-medical X-ray machine. As such, the invention is capable of performing its desired function when used in conjunction with commercial X-ray equipment.

In other embodiments, the initiation energy source 1 can be a radio frequency or microwave source emitting radio waves at a frequency which permeates the medium and which triggers or produces secondary radiant energy emission within the medium by interaction with the energy modulation elements 6 therein. In other embodiments, the initiation energy source 1 can be an ultraviolet, visible, near infrared (NIR) or infrared (IR) emitter emitting at a frequency which permeates the medium 4 and which triggers or produces secondary radiant energy emission within medium 4 by interaction with the energy modulation elements 6 therein.

Figure 3B:
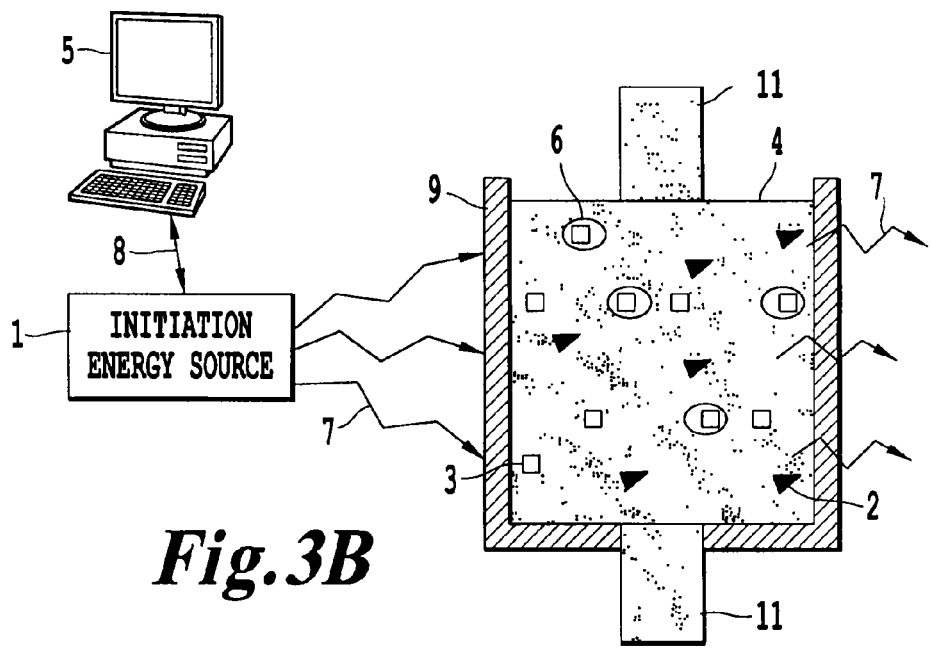
FIG. 3B is a schematic depicting a system according to another embodiment of the invention in which the initiation energy source is directed to a container enclosing a medium having energy modulation agents disbursed within the medium.

FIG. 3B is a schematic depicting another system according to another embodiment of the invention in which the initiation energy source 1 of FIG. 3A is directed to energy modulation elements 6 placed in the vicinity of a fluid medium 4 (e.g., a liquid or other fluid-like medium) and held inside a container 9. The container 9 is made of a material that is "transparent" to the radiation 7. For example, plastic, quartz, glass, or aluminum containers would be sufficiently transparent to X-rays, while plastic or quartz or glass containers would be transparent to microwave or radio frequency light. The energy modulation elements 6 can be dispersed uniformly throughout the medium or may be segregated in distinct parts of the medium or further separated physically from the medium by encapsulation structures 10. A supply 11 provides the medium 4 to the container 9.

Figure 3C:
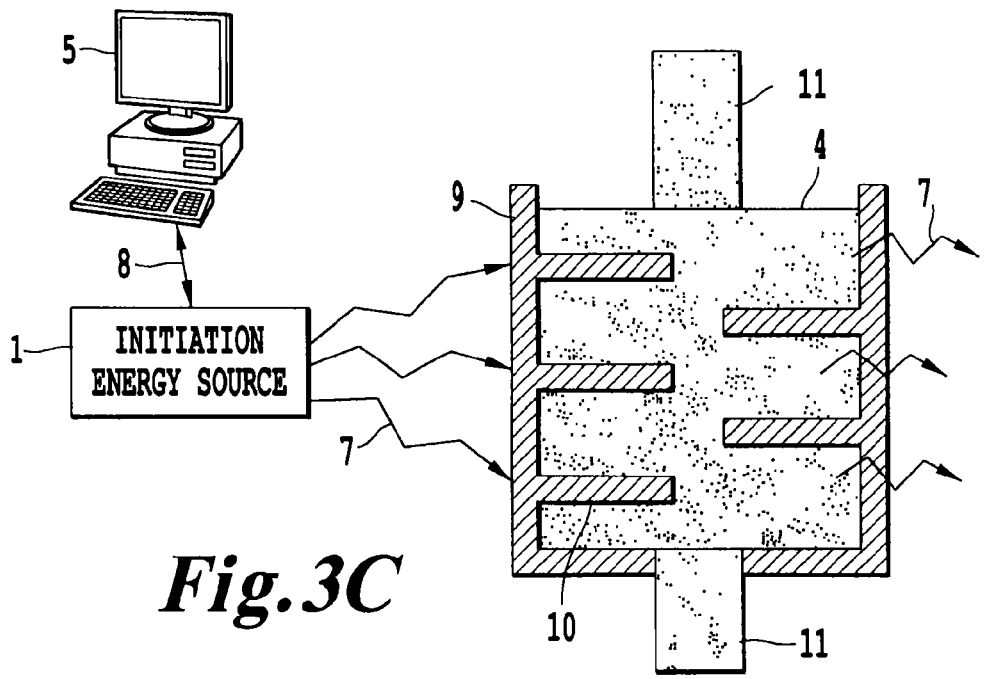
FIG. 3C is a schematic depicting a system according to another embodiment of the invention in which the initiation energy source is directed to a container enclosing a medium having energy modulation agents segregated within the medium.

Alternatively, as shown in FIG. 3C, the luminescing particles could be present in the medium in encapsulated structures 10. In one embodiment, the encapsulated structures 10 are aligned with an orientation in line with the external initiation energy source 1. In this configuration, each of the encapsulated structures 10 has itself a "line-of-sight" to the external initiation energy source 1 shown in FIG. 3C without being occluded by other of the encapsulated structures 10. In other embodiments, the encapsulated structures 10 are not so aligned in that direction, but could aligned perpendicular to the direction shown in FIG. 3C, or could be randomly placed. Indeed, supply of fluid medium 4 could itself be used to agitate the encapsulated structures 10 and mix the fluid medium 4 inside container 9.

The system of FIG. 3C may also be used without energy modulation agents. In this embodiment, the initiation energy source 1 can be for example at an energy suitable for driving physical, chemical, and/or biological processes in the fluid medium 4. In one aspect of the invention, the initiation energy source 1 can a UV light source as in many conventional UV sterilization systems and the encapsulated structures 10 of FIG. 3C are light rods conducting UV light from an exterior source to a region inside the medium 4. In one aspect of the invention, the initiation energy source 1 can be even disposed inside the medium and can be a UV light source as in many conventional UV sterilization systems.

Figure 3D:
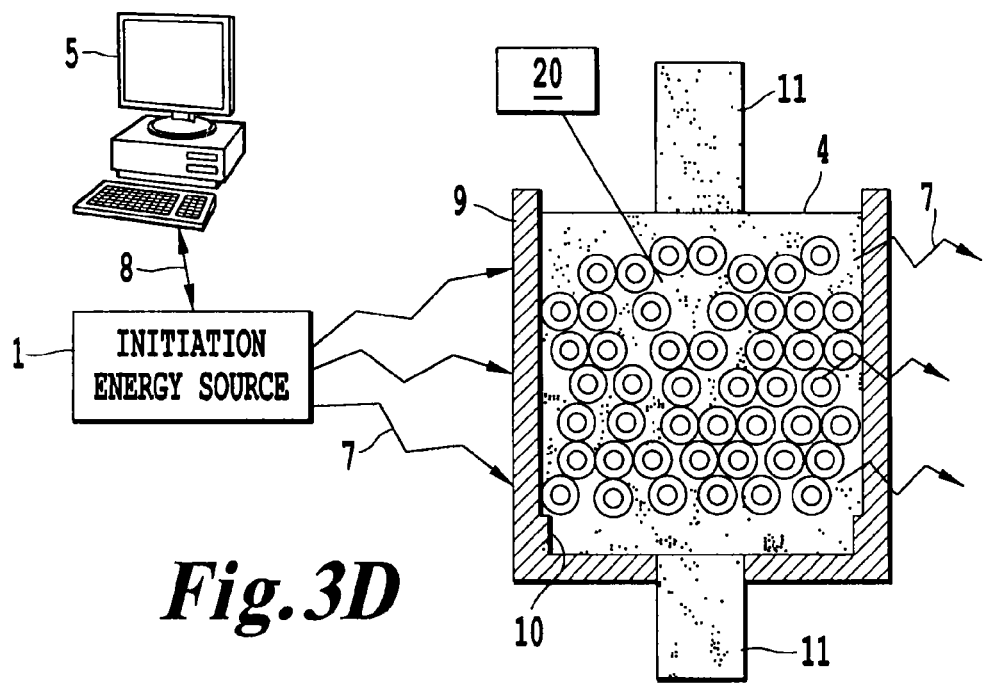
FIG. 3D is a schematic depicting a system according to another embodiment of the invention in which the initiation energy source is directed to a container enclosing a medium having energy modulation agents segregated within the medium in a fluidized bed configuration.

FIG. 3D is a schematic depicting a system according to another embodiment of the invention in which the initiation energy source is directed a container enclosing a medium having energy modulation agents segregated within the medium in a fluidized bed 20 configuration. The fluidized bed 20 includes the encapsulated structures 10 in a configuration where a fluid to be treated is passed between the encapsulated structures 10.

In further embodiments of the invention, robotic manipulation devices may also be included in the systems of FIGS. 3A, 3B, 3C, and 3D for the purpose of delivering and dispersing the energy modulation elements 6 in medium 4 or for the purpose of removing old product and introducing new product for treatment into the system.

Commercial Applications

In the following commercial applications of the invention described here, the energy modulation agents 3 (e.g., luminescing particles or photon emitters) are provided and distributed into a medium 4 for deactivation or activation of agents in the medium to produce a physical, chemical, or biological change in the medium.

Examples of luminescing particles can include gold particles (such as for example the nanoparticles of gold described above), BaFBr:Eu particles, CdSe particles, $Y_2O_3:Eu^{3+}$ particles, and/or other known stimulated luminescent materials such as for example $ZnS:Mn^{2+}$; $ZnS:Mn^{2+}, Yb^{3+}, Y_2O_3:Eu^{3+}$; $BaFBr:Tb^{3+}$; and $YF_3:Tb^3+$.

In one embodiment of the invention described here, other potentially useful luminescing particles (or energy modulation agents) include carbon nanotubes as described for example by Wang et al. in "Electromagnetic excitation of nano-carbon in vacuum," in OPTICS EXPRESS, Vol. 13, No. 10, May 10, 2005, the entire contents of which are incorporated herein by reference. Such carbon nanotubes show both black body emission and discrete line-type emissions in the visible when exposed to microwave irradiation.

Other potentially useful luminescing particles for the invention described here include the chemiluminescent reactions/species described by Aslan et al. in "Multicolor Microwave-Triggered Metal-Enhanced Chemiluminescence," in J. AM. CHEM. SOC. published on Web Sep. 23, 2006, the entire contents of which are incorporated herein by reference. These chemiluminescent reactions/species are formed with silver nanoparticles which enhance the chemiluminescent reactions when exposed to microwave radiation. Aslan et al. utilized chemiluminescent species from commercial glow sticks where for example hydrogen peroxide oxidizes phenyl oxalate ester to a peroxyacid ester and phenol. The unstable peroxyacid ester decomposes to a peroxy compound and phenol, the process chemically inducing an electronic excited state responsible for the light emission. While these chemiluminescent species will have a limited lifetime, there use in curing applications for the invention described here is still viable where the cure process is a one-time occurrence, and the external microwave source accelerates the cure by accelerated visible light production.

The luminescent wavelength and/or efficiency of the luminescent particles often depend on the size of the particle. Particle sizes in the nanometer size range for the invention described here exhibit stronger luminescence in many cases, as described in U.S. Pat. Appl. Publ. No. 2007/0063154, whose entire contents are incorporated herein by reference. Further, in one embodiment of the invention described here, the luminescing particles can be combined with molecular complexes such as poly(ethylene glycol), vitamin B12, or DNA, which serves to mitigate against coagulation of the luminescing particles (especially the nanoparticles) and serves to make the luminescing particles biocompatible. More specifically, one recipe for the synthesis of CdSe nanocrystals is given here from U.S. Pat. Appl. Publ. No. 2007/0063154. Accordingly, citrate-stabilized CdSe nanocrystals suitable for the invention described here can be prepared according to the following procedure:

To 45 ml of water are added 0.05 g sodium citrate (Fluka) and 2 ml of $4\times10^{-2}$M cadmium perchlorate (Aldrich). The pH is adjusted to 9.0 by 0.1 M NaOH (Alfa). The solution is bubbled with nitrogen for 10 minutes, and then 2 ml of $1\times10^{-2}$M N,N-dimethylselenourea (Alfa) is added. The mixture is heated in a conventional 900-watt microwave oven for 50 seconds. In this recipe, the Cd:Se molar ratio is 4:1, which leads to CdSe nanoparticles with ~4.0 nm diameter; by increasing the Cd concentration it is possible to synthesize smaller CdSe nanoparticles.

Further, the luminescing particles for the invention described here can be coated with insulator materials such as for example silica which will reduce the likelihood of any chemical interaction between the luminescing particles and the medium. For biological applications of inorganic nanoparticles, one of the major limiting factors is their toxicity. Generally speaking, all semiconductor nanoparticles are more or less toxic. For biomedical applications, nanoparticles with toxicity as low as possible are desirable or else the nanoparticles have to remain separated from the medium. Pure $TiO_2$, ZnO, and $Fe_2O_3$ are biocompatible. CdTe and CdSe are toxic, while ZnS, CaS, BaS, SrS and $Y_2O_3$ are less toxic. In addition, the toxicity of nanoparticles can result from their inorganic stabilizers, such as TGA, or from dopants such as $Eu^{2+}$, $Cr^{3+}$ or $Nd^{3+}$.

To reduce the toxicity or to make these nanoparticles bio-inert or biocompatible, one embodiment of the invention described here coats these nanoparticles with silica. Silica is used as a coating material in a wide range of industrial colloid products from paints and magnetic fluids to high-quality paper coatings. Further, silica is both chemically and biologically inert and also is optically transparent. In the following recipe (from M A. Correa-Duarte, M Giesig, and L. M Liz-Marzan, *Stabilization of CdS semiconductor nanoparticles against photodegradation by a silica coating procedure*, Chem. Phys. Lett., 1998, 286: 497, the entire contents of which is explicitly incorporated herein by reference in its entirety), citrate-stabilized CdTe:Mn 2+/$SiO_2$ nanocrystals suitable for the invention described here can be prepared with a silica coating:

(1) To a CdTe:Mn 2+ nanoparticle solution (50 ml), a freshly prepared aqueous solution of 3-(mercaptopropyl)trimethoxysilane (MPS) (0.5 ml, 1 mM) (Sigma) is added under vigorous stirring. The function of MPS is that its mercapto group can directly bond to the surface Cd sites of CdTe, while leaving the silane groups pointing toward solution from where silicate ions approach the particle surface; (2) Addition of 2 ml of sodium silicate (Alfa) solution at pH of 10.5 under vigorous stirring; (3) The resulting dispersion (pH ~8.5) is allowed to stand for 5 days, so that silica slowly polymerizes onto the particle surface; and (4) Transfer of the dispersion to ethanol so that the excess dissolved silicate can precipitate out, increasing the silica shell thickness.

Alternatively, as shown in FIG. 3C and FIG. 3D, luminescing particles in encapsulated structures 10 could be placed in the vicinity of the medium. In one embodiment for the invention described here, luminescing particles are coated on the interior of quartz or glass tubes 9 and sealed. In another embodiment, luminescing particles could be coated on the surface of spheres or tubes, and afterwards encapsulated with silica (or other suitable passivation layer) using a vapor deposition or sputtering process or spin-on glass process of the solution process described above to make the encapsulation structures 10 which may be part of re-entrant structures extending from walls of a container (as in FIG. 3C) or which may be part of a fluidized bed structure (as in FIG. 3D).

In the either configuration, the medium to be treated would flow by the encapsulated structures 10, or flow along with encapsulated structures 6, and the separation distance between the encapsulated structures 6, 10 would be set a distance smaller than the UV penetration depth in the medium.

A suitable light source (such as one of the x-ray sources discussed above) can be used to stimulate the luminescing particles in the encapsulated structures 10. In one embodiment of the invention described here, the concentration of luminescing particles in the medium or the spacing between the encapsulated structures 10 is set such that luminescing particles are separated from each other in the medium by less than a UV depth of penetration into the medium. Higher concentrations are certainly usable and will generate higher UV fluxes should the energy source have enough intensity to "light" all the luminescing particles.

For a relatively unclouded aqueous medium, solar UV-B irradiance decreases to 1% after penetration into the water samples between 0.2 m and 1 m, whereas UV-A penetrates on the order of several meters. For such mediums, the concentration of luminescing particles is more determined by the time needed for the intended UV flux to produce deactivation or activation of an agent in the medium, rather than having to be set based on a concentration of luminescent particles where the medium itself does not occlude the UV stimulated emission from penetrating throughout the medium. The placement of the luminescent particles in the medium and in the vicinity of the medium is not restricted by the optical density of the medium.

Based on published data of an average of 5.2 spontaneous photons emitted from BaFBr:$Eu^{2+}$ for every keV of X-ray absorbed (M. Thorns, H von Seggern, *Method for the determination of photostimulable defect center concentrations, production rates, and effective formation energies*, J. Appl. Phys. 1994, 75: 4658-4661, the entire contents of which is herein explicitly incorporated by reference in its entirety.), one expects that about 50 photons are emitted from a CdTe nanoparticle for each 50 keV X-ray absorbed.

Based on the results in U.S. Pat. Appl. Publ. No. 2007/0063154 for X-ray spectra of CdTe/BaFBr:$Eu^{2+}$ nanocomposites prepared using a concentration of 0.8 ml L-cysteine stabilized CdTe particle solution in 0.2 g BaFBr:$Eu^{2+}$ phosphor. As the X-ray irradiation time increases, the X-ray luminescence intensity of $Eu^{2+}$ at 390 nm increases in intensity. This phenomenon has been discussed in W. Chen, S. P. Wang, S. Westcott, J. Zhang, A. G. Joly, and D. E. McCready, *Structure and luminescence of BaFBr:$Eu^{2+}$ and BaFBr:$Eu^{2+}$, $Tb^{3+}$ phosphors and thin films*, J. Appl. Phys. 2005, 97: 083506, the entire contents of these references are herein incorporated by reference in their entirety.

Hence, in one embodiment of the invention, a minimum baseline concentration of about $10^9$ nanoparticles per $cm^3$ for 200 nm diameter particles is expected to be sufficient for UV emission to produce a change in the medium. The invention is not limited to this concentration range, but rather this range is given as an illustrative example. Indeed, higher concentrations will increase the UV emission per unit time and provide faster reactions, which in general would be considered more useful in industrial applications where product throughput is a concern.

Sterilization and Cold Pasteurization of Fluids

Table 1 included below shows appropriate intensities for germicidal destruction.

TABLE 1

Germicidal energies needed to destroy
Approximate intensity ($\mu W/cm^2$) required for
99% destruction of microorganisms:

| | |
|---|---|
| Bacteria | 10 400 |
| Protozoa (single celled organism) | 105 000 |
| Paramecium (slipper shaped protozoa) | 200 000 |
| Chlorella (unicellular fresh-water alga) | 13 000 |
| Flagellate(protozoan or alga with flagella) | 22 000 |
| Sporozoan (parasitic protozoans) | 100 000 |
| Virus | 8 000 |

Accordingly, the energy modulation agents (or luminescing particles) of the invention (as discussed above with regard to FIGS. 3B and 3C) can be provided on the interior of sealed quartz or glass tubes or can be provided coated on the surface of spheres or tubes, and further encapsulated with a silica or passivation layer. In either configuration for the invention described here, a medium could flow by the encapsulated structures 6, 10 with a separation distance between the encapsulated structures or the quartz or glass tubes being made smaller than the UV penetration depth.

For example, it is known that ultraviolet (UV) with a wavelength of 254 nm tends to inactivate most types of microorganisms. Most juices are opaque to UV due to the high-suspended solids in them and hence the conventional UV treatment, usually used for water treatment, cannot be used for treating juices. In order to make the process efficient, a thin film reactor constructed from glass has been used with the juice flowing along the inner surface of a vertical glass tube as a thin film. See "Ultraviolet Treatment of Orange Juice" by Tran et al. published in Innovative Food Science & Emerging Technologies (Volume 5, Issue 4, December 2004, Pages 495-502), the entire contents of which are incorporated herein by reference. Tran et al. reported therein decimal reduction doses required for the reconstitute orange juices (OJ; 10.5° Brix) were 87±7 and 119±17 $mJ/cm^2$ for the standard aerobic plate count (APC) and yeast and moulds, respectively. In that article, the shelf life of fresh squeezed orange juice was extended to 5 days with a limited exposure of UV (73.8 $mJ/cm^2$). The effect of UV on the concentration of Vitamin C was investigated using both HPLC and titration methods of measurements. The degradation of Vitamin C was 17% under high UV exposure of 100 $mJ/cm^2$, which was similar to that usually found in thermal sterilization. Enzyme pectin methylesterase (PME) activity, which is the major cause of cloud loss of juices, was also measured. The energy required for UV treatment of orange juice (2.0 kW $h/m^3$) was much smaller than that required in thermal treatment (82 kW $h/m^3$). The color and pH of the juice were not significantly influenced by the treatment.

The invention described herein offers advantages over this approach in that the energy modulation agents can be placed inside fixtures such as quartz or glass (encapsulation structures 8) within the orange juice (or other fluid medium) and irradiated with x-rays (or other penetrating radiation) through for example a plastic or aluminum container 9 to activate the energy modulation agents 3 and 6 in the orange juice. As such, the expense and fragility of a thin film reactor constructed from glass of other similar structure is avoided.

While discussed with regard to orange juice, any other medium to be sterilized including food products, medical products and cosmetic products could be treated using the technique of the invention described herein.

Sterilization of Medical and Pharmaceutical Articles

As noted above, medical bottle caps need to be sterilized between the base cap material and the seal material which contacts to the base of the medical bottle. Steam autoclaves are insufficient for this purpose as once glued, the steam is unable to penetrate into the glue seam.

Gamma irradiation has been used conventionally to sterilize medical bottle caps and other medical, pharmaceutical, and cosmetic articles such as surgical disposables (e.g., surgical bandages, dressings, gauge pads, nappies, delivery kits, and etc.), metallic products (e.g., surgical blades, implants, aluminum caps, containers, etc.), and plastic and rubber Items (e.g., petri-dish, centrifuge tube, blood collection sets, scalp vein sets, shunt valves, rubber gloves, contraceptive devices, gowns, wraps covers, sheets, etc.). The invention would be applicable for the sterilization of any "interior" surfaces of these and other products.

In one embodiment of the invention described herein, UV luminescent particles would be included in an adhesive layer when the seal material is applied to the bottle cap. X-ray irradiation would then be capable of curing the adhesive (if for example the adhesive were a photosensitive adhesive as discussed below in greater detail) and would produce within the adhesive medium UV radiation for direct sterilization or for the production of singlet oxygen or ozone for biological germicide.

While illustrated here with regard to medical bottle caps, other adhesively constructed devices could benefit from these procedures in which the adhesive medium is cured and/or sterilized during activation of energy modulation agents 3 and 6.

Sterilization of Blood Products

U.S. Pat. No. 6,087,141 (the entire contents of which are incorporated herein by reference) describes an ultraviolet light actived psoralen process for sterilization of blood transfusion products. Here, the invention can be applied for example in the equipment shown in FIGS. 3C and 3D for the treatment of or the neutralization of AIDS and HIV or other viral or pathogenic agents in blood transfusion products. In this embodiment, at least one photoactivatable agent is selected from psoralens, pyrene cholesteryloleate, acridine, porphyrin, fluorescein, rhodamine, 16-diazorcortisone, ethidium, transition metal complexes of bleomycin, transition metal complexes of deglycobleomycin organoplatinum complexes, alloxazines, vitamin Ks, vitamin L, vitamin metabolites, vitamin precursors, naphthoquinones, naphthalenes, naphthols and derivatives thereof having planar molecular conformations, porphorinporphyrins, dyes and phenothiazine derivatives, coumarins, quinolones, quinones, and anthroquinones. These photoactivatable agents are introduced into the blood product (or a patient's blood stream). A penetrating energy is applied to the blood product (or to the patient). The energy modulation agents (either included in the blood product) or in encapsulated structures 10 generate secondary light such as UV light which activates the photoactivatable agents in the blood products.

In a specific example, the photoactivatable agent is a psoralen, a coumarin, or a derivative thereof, and as discussed above, one can sterilize blood products in vivo (i.e., in a patient) or in a container of the blood product (such as for example donated blood). The treatment can be applied to treat disorders such as for example a cancer cell, a tumor cell, an autoimmune deficiency symptom virus, or a blood-borne germicide is treated by the psoralen, the coumarin, or the derivative thereof.

Waste Water Detoxification

Photocatalysis has also been used as tertiary treatment for wastewater to comply with the regulatory discharge limits and to oxidize persistent compounds that have not been oxidized in the biological treatment. Photocatalysis has being applied to the elimination of several pollutants (e.g., alkanes, alkenes, phenols, aromatics, pesticides) with great success.

In many cases, total mineralization of the organic compounds has been observed. Several photocatalysts, such as $CdS$, $Fe_2O_3$, $ZnO$, $WO_3$, and $ZnS$, have been studied, but the best results have been achieved with $TiO_2P_{25}$. These photocatalyst are usable for the invention described here.

The wastewaters of an oil refinery are the waters resulting from washing the equipment used in the process, undesirable wastes, and sanitary sewage. These effluents have high oil and grease contents, besides other organic compounds in solution. These pollutants form a residual chemical oxygen demand (COD) that may pose serious toxic hazards to the environment.

It is known that photocatalysis can be used for waste water reduction remediation. U.S. Pat. No. 5,118,422 (the entire contents of which are incorporated herein by reference) to Cooper et al. describe an ultraviolet driven photocatalytic post-treatment technique for purifying a water feedstock containing an oxidizable contaminant compound. In this work, the water feedstock was mixed with photocatalytic semiconductor particles (e.g., $TiO_2$, $ZnO$, $CdS$, $CdSe$, $SnO_2$, $SrTiO_3$, $WO_3$, $Fe_2O_3$, and $Ta_2O_5$ particles) having a particle size in the range of about 0.01 to about 1.0 micron and in an amount of between about 0.01% and about 0.2% by weight of the water. The water including the semiconductor mixture is exposed to band-gap photons for a time sufficient to effect an oxidation of the oxidizable contaminant to purify the water. Crossflow membrane filtration was used to separate the purified water from the semiconductor particles. Cooper et al. show that the organic impurity carbon content of simulated reclamation waters at nominal 40 PPM level were reduced to parts per billion using a recirculation batch reactor.

Cooper et al. identified that one important aspect of the photocatalytic process is the adsorption of the organic molecules onto the extremely large surface area presented by the finely divided powders dispersed in the water. Cooper et al. further indicated that, in photoelectrochemical applications, advantage is taken of the fact that the solid phase (a metal oxide semiconductor) is also photo-active and that the generated charge carriers are directly involved in the organic oxidation. The adsorption of the band-gap photon by the semiconductor particle results in the formation of an electron ($e^-$)/hole($h^+$) pair. Cooper et al. explain that the electrons generated in the conduction band react with solution oxygen forming the dioxygen anion ($O_{2-}$) species which subsequently undergo further reactions resulting in the production of the powerfully oxidizing hydroxyl radical species, OH. These powerful oxidants are known to oxidize organic compounds by themselves. Additionally, Cooper et al. explain that the strongly oxidizing holes generated in the valence band have sufficient energy to oxidize all organic bonds.

In the reactor of Cooper et al., turbulence is necessary in order to ensure that the waste water contaminants and the photocatalytic titania particles are exposed to the UV light. Cooper et al. explain that the most basic considerations of photocatalyst light adsorption and its relationship to convective mixing. For a 0.1 wt % photocatalyst loading, experiments have shown that 90% of the light is absorbed within 0.08 cm. This is primarily due to the large UV absorption coefficient of the photocatalyst and therefore, most of the photoelectrochemistry occurs within this illuminated region. By operating the reactor of Cooper et al. with a Reynolds number (Re) of 4000, a significant portion of the photoactive region is ensured of being within the well mixed turbulent zone.

Santos et al. have reported in "Photocatalysis as a tertiary treatment for petroleum refinery wastewaters" published in Braz. J. Chem. Eng. vol. 23, No. 4, 2006 (the entire contents of which are incorporated herein by reference), photocatalysis for tertiary treatment for petroleum refinery wastewaters which satisfactorily reduced the amount of pollutants to the level of the regulatory discharge limits and oxidized persistent compounds that had not been oxidized in the biological treatment. The treatment sequence used by the refinery (REDUC/PETROBRAS, a Brazilian oil refinery) is oil/water separation followed by a biological treatment. Although the process efficiency in terms of biological oxygen demand (BOD) removal is high, a residual and persistent COD and a phenol content remains. The refining capacity of the refinery is 41,000 $m^3$/day, generating 1,100 $m^3$/h of wastewater, which are discharged directly into the Guanabara Bay (Rio de Janeiro). Treating the residual and persistent COD remains a priority.

Santos et al. conducted a first set of experiments carried out in an open 250 mL reactor containing 60 mL of wastewater. In the second set of experiments, a Pyrex® annular reactor containing 550 mL of wastewater was used (De Paoli and Rodrigues, 1978), as shown in FIG. 1. The reaction mixtures inside the reactors were maintained in suspension by magnetic stirring. In all experiments, air was continuously bubbled through the suspensions. A 250 W Phillips HPL-N medium pressure mercury vapor lamp (with its outer bulb removed) was used as the UV-light source (radiant flux of 108 $J \cdot m^{-2} \cdot s^{-1}$ at 8>254 nm). In one set of experiments, the lamp was positioned above the surface of the liquid at a fixed height (12 cm). In the second set, the lamp was inserted into the well. All experiments by Santos et al. were performed at 25±1° C. The catalyst concentration ranged from 0.5 to 5.5 g $L^{-1}$ and the initial pH ranged from 3.5 to 9.

In the invention described herein, luminescing particles or other energy modulation agents would be placed inside quartz or glass fixtures within the waste water or would be placed on silica encapsulated structures within the waste water which, like the photocatalytic $TiO_2$, could be entrained in the waste water during the irradiation.

Upon irradiation with x-rays (or other penetrating radiation) through for example a plastic or aluminum container, activation of the luminescing particles (i.e., energy modulation agents) would generate UV light in nearby presence of the photocatalytic agent. In other words for the invention described herein, the luminescent particles or other energy modulation agents are mixed along with the photocatalytic semiconductor particles in the waste water fluid stream, and the exterior activation energy source penetrates the container (e.g., a plastic or aluminum container) and irradiates the bulk of the waste water, producing UV light throughout the waste water which in turn drives the photocatalytic reactions.

As such, the invention described herein offers a number to advantages over that described above, including the elimination of expensive holding tanks for the waste water, the avoidance of having to pump the wastewater at higher pressures or flowrates to produce sufficient turbulence, and the generation of UV light throughout the wastewater to thereby provide faster bulk processing of the waste water.

Photostimulation

Photostimulation is a field in which light is applied to in order to alter or change a physical property. For example, there has been an increased focus on the use of biodegradable polymers in consumer and biomedical fields. Polylactic acid (PLA) plastics and polyhydroxyalkanoates (PHA) plastics have been playing a vital role in fulfilling the objectives. But their relatively hydrophobic surfaces limit their use in various applications. Hence, there is a need to surface modify these film surfaces. Due to the lack of any modifiable side chain groups, workers have used a sequential two step photografting technique for the surface modification of these biopolymers. In step one, benzophenone was photografted on the film surface and in step two, hydrophilic monomers like acrylic acid and acrylamide were photopolymerized from the film surfaces.

Workers have found that UV irradiation could realize an effective graft copolymerization. UV-assisted photografting in ethanol has been used to grow hydrophilic polymers (e.g., poly(acrylic acid) and polyacrylamide) from the surfaces of PLA, PHA, and PLA/PHA blend films. In that work, a functional polyurethane (PU) surface was prepared by photografting N,N-dimethylaminoethyl methacrylate (DMAEM) onto the membrane surface. Grafting copolymerization was conducted by the combined use of the photo-oxidation and irradiation grafting. PU membrane was photo-oxidized to introduce the hydroperoxide groups onto the surface, then the membrane previously immersed in monomer solution was irradiated by UV light. Results have shown prior to the invention that UV irradiation can realize graft copolymerization effectively.

In the invention described herein, these processes are expedited by the inclusion of luminescing particles or other energy modulation agents in dispersion in the fluid medium being used for photostimulation.

Upon irradiation with x-rays (or other penetrating radiation) through for example a plastic or aluminum container, activation of the luminescing particles (i.e., energy modulation agents) would generate UV light throughout the volume of the medium (eliminating any shadowing effects) and permitting batch or bulk type processing to occur in parallel throughout the container.

In other examples, the interior generation of light inside a bulk medium may serve to stimulate a chemical or biological process either by direct interaction of the light with activatable agents in the medium or the indirect generation of heat which the invention described here by way of dispersed energy modulation agents would provide a controlled and uniform way to heat a vat of material in a biological or chemical process.

Photodeactivation

In many industrial processes, especially food and beverage industries, yeasts are used to produce changes in a medium such as the conversion of sugars in the raw product. One particularly prominent example is in the wine industry. Stopping the wine from fermenting any further would preserve the current level of sweetness. Likewise, allowing the wine to continue fermenting further would only make the wine less sweet with each passing day. Eventually the wine would become completely dry at which time the fermentation would stop on its own. This is because during the fermentation process yeast turns the sugar into alcohol.

Wanting to stop a fermentation is all good in and of itself. But unfortunately, there is really no practical way to successfully stop a fermentation dead in its tracks. Additives such as sulphite and sorbate can be added to stabilize a fermented product and stop additional fermentation. Many winemakers will turn to sulfites such as that found in Sodium Bisulfite or Campden tablets for the answer. But, these two items are not capable of reliably killing enough of the yeast to guarantee a complete stop of the activity—at least not at normal doses that leave the wine still drinkable.

Once the bulk of the sulfites from either of these ingredients dissipate from the wine into the air—as sulfites do—there is a very strong chance that the remaining few live yeast cells will start multiplying and fermenting again if given enough time. This usually happens at a most inconvenient time, like after the wine has been bottled and stowed away.

Potassium sorbate is another ingredient that many winemakers consider when trying to stop a wine from fermenting any further. There is a lot of misunderstanding surrounding this product. It is typically called for by home wine making books when sweetening a wine. This is a situation where the fermentation has already completed and is ready for bottling. One adds the potassium sorbate along with the sugar that is added for sweetening.

The potassium sorbate stops the yeast from fermenting the newly added sugar. So, many winemakers assume potassium sorbate can stop an active fermentation as well, but, potassium sorbate does not kill the yeast at all, but rather it makes the yeast sterile. In other words, it impairs the yeast's ability to reproduce itself. But, it does not hinder the yeast's ability to ferment sugar into alcohol.

Ultraviolet light is known to destroy yeast cultures, but has restricted applications due to the inability of UV light to penetrate throughout the fluid medium. While heat can be used to destroy the yeast activity, cooking of the product may be premature or may produce undesirable changes in the consistency and taste. For liquid or fluid food products, the same techniques described above for liquid pasteurization could be used for the invention described here. For non-liquid products, energy modulation agents with little and preferably no toxicity (e.g. Fe oxides or titanium oxides) could be added. Here, the concentration of these additives would likely be limited by any unexpected changes in taste.

Photoactivated Cross-linking and Curing of Polymers

In this application, luminescing particles (or energy modulation agents) are provided and distributed into an uncured polymer based medium for the activation of photosensitive agents in the medium to promote cross-linking and curing of the polymer based medium.

As noted above, for adhesive and surface coating applications, light activated processing is limited due to the penetration depth of UV light into the processed medium. In light activated adhesive and surface coating processing, the primary limitation is that the material to be cured must see the light—both in type (wavelength or spectral distribution) and intensity. This limitation has meant that one medium typically has to transmit the appropriate light. In adhesive and surface coating applications, any "shaded" area will require a secondary cure mechanism, increasing cure time over the non-shaded areas and further delaying cure time due to the existent of a sealed skin through which subsequent curing must proceed.

Conventionally, moisture-curing mechanisms, heat-curing mechanisms, and photo-initiated curing mechanisms are used to initiate cure, i.e., cross-linking, of reactive compositions, such as reactive silicones, polymers, and adhesives. These mechanisms are based on either condensation reactions, whereby moisture hydrolyzes certain groups, or addition reactions that can be initiated by a form of energy, such as electromagnetic radiation or heat.

The invention described herein can use any of the following light activated curing polymers as well as others known in the art to which the luminescing particles (or energy modulation agents) are added.

For example, one suitable light activated polymer compound includes UV curing silicones having methacrylate functional groups. U.S. Pat. No. 4,675,346 to Lin, the disclosure of which is hereby expressly incorporated herein by reference, is directed to UV curable silicone compositions including at least 50% of a specific type of silicone resin, at least 10% of a fumed silica filler and a photoinitiator, and cured compositions thereof. Other known UV curing silicone compositions suitable for the invention include organopolysiloxane containing a (meth)acrylate functional group, a photosensitizer, and a solvent, which cures to a hard film. Other known UV curing silicone compositions suitable for the invention include compositions of an organopolysiloxane having an average of at least one acryloxy and/or methacryloxy group per molecule; a low molecular weight polyacrylyl crosslinking agent; and a photosensitizer.

Loctite Corporation has designed and developed UV and UV/moisture dual curable silicone compositions, which also demonstrate high resistance to flammability and combustibility, where the flame-retardant component is a combination of hydrated alumina and a member selected from the group consisting of organo ligand complexes of transition metals, organosiloxane ligand complexes of transition metals, and combinations thereof. See U.S. Pat. Nos. 6,281,261 and 6,323,253 to Bennington. These formulations are also suitable for the invention.

Other known UV photoactivatable silicones include silicones functionalized with for example carboxylate, maleate, cinnamate and combinations thereof. These formulations are also suitable for the invention. Other known UV photoactivatable silicones suitable for the invention include benzoin ethers ("UV free radical generator") and a free-radical polymerizable functional silicone polymers, as described in U.S. Pat. No. 6,051,625 whose content is incorporated herein by reference in its entirety. The UV free radical generator (i.e., the benzoin ether) is contained at from 0.001 to 10 wt % based on the total weight of the curable composition. Free radicals produced by irradiating the composition function as initiators of the polymerization reaction, and the free radical generator can be added in a catalytic quantity relative to the polymerizable functionality in the subject composition. Further included in these silione resins can be silicon-bonded divalent oxygen atom compounds which can form a siloxane bond while the remaining oxygen in each case can be bonded to another silicon to form a siloxane bond, or can be bonded to methyl or ethyl to form an alkoxy group, or can be bonded to hydrogen to form silanol. Such compounds can include trimethylsilyl, dimethylsilyl, phenyldimethylsilyl, vinyldimethylsilyl, trifluoropropyldimethylsilyl, (4-vinylphenyl)dimethylsilyl, (vinylbenzyl)dimethylsilyl, and (vinylphenethyl)dimethylsilyl.

The photoinitiator component of the invention is not limited to those free radical generators given above, but may be any photoinitiator known in the art, including the afore-mentioned benzoin and substituted benzoins (such as alkyl ester substituted benzoins), Michler's ketone, dialkoxyacetophenones, such as diethoxyacetophenone ("DEAP"), benzophenone and substituted benzophenones, acetophenone and substituted acetophenones, and xanthone and substituted xanthones. Other desirable photoinitiators include DEAP, benzoin methyl ether, benzoin ethyl ether, benzoin isopropyl ether, diethoxyxanthone, chloro-thio-xanthone, azo-bisisobutyronitrile, N-methyl diethanolaminebenzophenone, and mixtures thereof. Visible light initiators include camphoquinone, peroxyester initiators and non-fluorene-carboxylic acid peroxyesters.

Commercially available examples of photoinitiators suitable for the invention include those from Vantico, Inc., Brewster, N.Y. under the IRGACURE and DAROCUR tradenames, specifically IRGACURE 184 (1-hydroxycyclohexyl phenyl ketone), 907 (2-methyl-1-[4-(methylthio)phenyl]-2-morpholino propan-1-one), 369 (2-benzyl-2-N,N-dimethylamino-1-(4-morpholinophenyl)-1-butanone), 500 (the combination of 1-hydroxy cyclohexyl phenyl ketone and benzophenone), 651 (2,2-dimethoxy-2-phenyl acetophenone), 1700 (the combination of bis(2,6-dimethoxybenzoyl-2,4,4-trimethyl pentyl)phosphine oxide and 2-hydroxy-2-methyl-1-phenyl-propan-1-one), and 819 [bis(2,4,6-trimethyl benzoyl)phenyl phosphine oxide] and DAROCUR 1173 (2-hydroxy-2-methyl-1-phenyl-1-propane) and 4265 (the combination of 2,4,6-trimethylbenzoyldiphenyl-phosphine oxide and 2-hydroxy-2-methyl-1-phenyl-propan-1-one); and IRGACURE 784DC (bis(.eta..sup.5-2,4-cyclopentadien-1-yl)-bis[2,6-difluoro-3-(1H-pyrrol-1-yl)phenyl] titanium).

Generally, the amount of photoinitiator (or free radical generators) should be in the range of about 0.1% to about 10% by weight, such as about 2 to about 6% by weight. The free radical generator concentration for benzoin ether is generally from 0.01 to 5% based on the total weight of the curable composition.

A moisture cure catalyst can also be included in an amount effective to cure the composition. For example, from about 0.1 to about 5% by weight, such as about 0.25 to about 2.5% by weight, of the moisture cure catalyst can be used in the invention to facilitate the cure process beyond that of photoactivated curing. Examples of such catalysts include organic compounds of titanium, tin, zirconium and combinations thereof. Tetraisopropoxytitanate and tetrabutoxytitanate are suitable as moisture cure catalyst. See also U.S. Pat. No. 4,111,890, the disclosure of which is expressly incorporated herein by reference.

Included in the conventional silicone composition (and other inorganic and organic adhesive polymers) suitable for the invention are various inorganic fillers. For example, hollow microspheres supplied by Kish under the trade name Q-CEL are free flowing powders, white in color. Generally, these borosilicate hollow microspheres are promoted as extenders in reactive resin systems, ordinarily to replace heavy fillers, such as calcium carbonate, thereby lowering the weight of composite materials formed therewith. Q-CEL 5019 hollow microspheres are constructed of a borosilicate, with a liquid displacement density of 0.19 g/cm$^2$, a mean particle size of 70 microns, and a particle size range of 10-150 urn. Other Q-CEL products are shown below in tabular form. Another commercially available hollow glass microsphere is sold by Kish under the trade name SPHERICEL. SPHERICEL 110P8 has a mean particle size of about 11.7 microns, and a crush strength of greater than 10,000 psi. Yet other commercially available hollow glass microsphere are sold by the Schundler Company, Metuchen, N.J. under the PERLITE tradename, Whitehouse Scientific Ltd., Chester, UK and 3M, Minneapolis, Minn. under the SCOTCHLITE tradename.

In general, these inorganic filler components (and others such as fumed silica) add structural properties to the cured composition, as well as confers flowability properties to the composition in the uncured state and increase the transmissivity for the UV cure radiation. When present, the fumed silica can be used at a level of up to about 50 weight percent, with a range of about 4 to at least about 10 weight percent, being desirable. While the precise level of silica may vary depending on the characteristics of the particular silica and the desired properties of the composition and the reaction product thereof, care should be exercised by those persons of ordinary skill in the art to allow for an appropriate level of transmissivity of the inventive compositions to permit a UV cure to occur.

Desirable hydrophobic silicas include hexamethyldisilazane-treated silicas, such as those commercially available from Wacker-Chemie, Adrian, Mich. under the trade designation HDK-2000. Others include polydimethylsiloxane-treated silicas, such as those commercially available from Cabot Corporation under the trade designation CAB—O-SIL N70-TS, or Degussa Corporation under the trade designation AEROSIL 8202. Still other silicas include trialkoxyalkyl silane-treated silicas, such as the trimethoxyoctyl silane-treated silica commercially available from Degussa under the trade designation AEROSIL R805; and 3-dimethyl dichlorosilane-treated silicas commercially available from Degussa under the trade designation R972, R974 and R976.

While these inorganic fillers have extended the use of conventional UV cured silicone systems to permit the curing of materials beyond a skin depth of UV penetration, these inorganic fillers alone do not overcome shadowing effects and suffer from UV scattering which effectively makes for a smaller penetration depth. In the invention described herein, the inclusion of these inorganic fillers along with luminescing particles provide a mechanism by which uniform light activated cures can occur deep inside of the body of adhesive-solidified assemblies in regions that would normally be shadowed or not with the reach of external UV or other light sources.

Accordingly, in this example of the invention described herein, conventional silicone and polymeric adhesive or release or coating compositions are prepared using conventional mixing, heating, and incubation techniques. Included in these conventional compositions are luminescing particles. These luminescing particle containing compositions can then be applied to surfaces of objects to be fixed together or to surfaces where a hard coating is desired or cast in a curable form for the production of molded objects. The luminescing particles in these compositions upon activation will produce radiant light for photoactivated cure of the luminescing particle containing polymer composition. The density of luminescing particles in these compositions will depend on the "light transparency" of the luminescing particle containing composition. Where these compositions contain a significant amount of the inorganic filler as discussed above, the concentration of luminescing particles can be reduced for example as compared to a composition with a black color pigment where the light transparency will be significantly reduced.

One advantage of the invention described here as seen from this example is that now color pigments can be included in the light curable resins without significant compromise in the cured product performance. These color pigments may include one or more colored pigments well known to those of ordinary skill in the art. Such pigments are generally metal oxides and include, but are not limited to, titanium dioxide, iron oxides, organic complexes, mica, talc and quartz. One pigment may be used, or a combination of two or more pigments may be utilized. Different colors can be obtained by choosing proper pigments and combining them in a similar fashion as set forth in the following examples with the necessary adjustments, common in the paint industry, being made. Accordingly, in one embodiment of the invention, these color pigments including carbon black may also be included as an optically opaque materials to limit the propagation of internally generated light from the point of generation.

U.S. Pat. No. 7,294,656 to Bach et al., the entire disclosure of which is incorporated herein by reference, describes a non-aqueous composition curable by UV radiation broadly containing a mixture of two UV curable urethane acrylates that have several advantages over conventional radiation-curable compositions. The Bache et al. compositions can be cured in a relatively short time using UV-C (200-280 nm), UV-B (280-320 nm), UV-A (320-400 nm) and visible (400 nm and above) radiation. In particular, Bache et al. compositions can be cured using radiation having a wavelength of 320 nm or more. When fully cured (regardless of the type of radiation used), the Bach et al. compositions exhibit hardnesses and impact resistances at least comparable to conventional coatings.

In the invention described here, the luminescing particles (or energy modulation agents) described above are added to these Bach et al. compositions, optionally including in one embodiment various color pigments. Due to the fact that the exterior energy source penetrates throughout the entirety of the Bach et al. compositions, thicker surface coatings can be realized. Further, the coatings can be applied to intricate surfaces having for example been prepared with recesses or protrusions. Curing with the recesses and around the protrusions without being limited by conventional UV shading will likely provide enhanced adherence of the surface coating to the work piece.

Computer-Assisted Control

In one embodiment of the invention, there is provided a computer implemented system for designing and selecting suitable combinations of initiation energy source, energy modulation agent, and activatable agent. For example, the computer system 5 can include a central processing unit (CPU) having a storage medium on which is provided: a database of excitable compounds, a first computation module for a photoactivatable agent or energy transfer agent, and a second computation module predicting the requisite energy flux needed to sufficiently activate the or energy transfer agent or photoactivatable agent.

Figure 4:
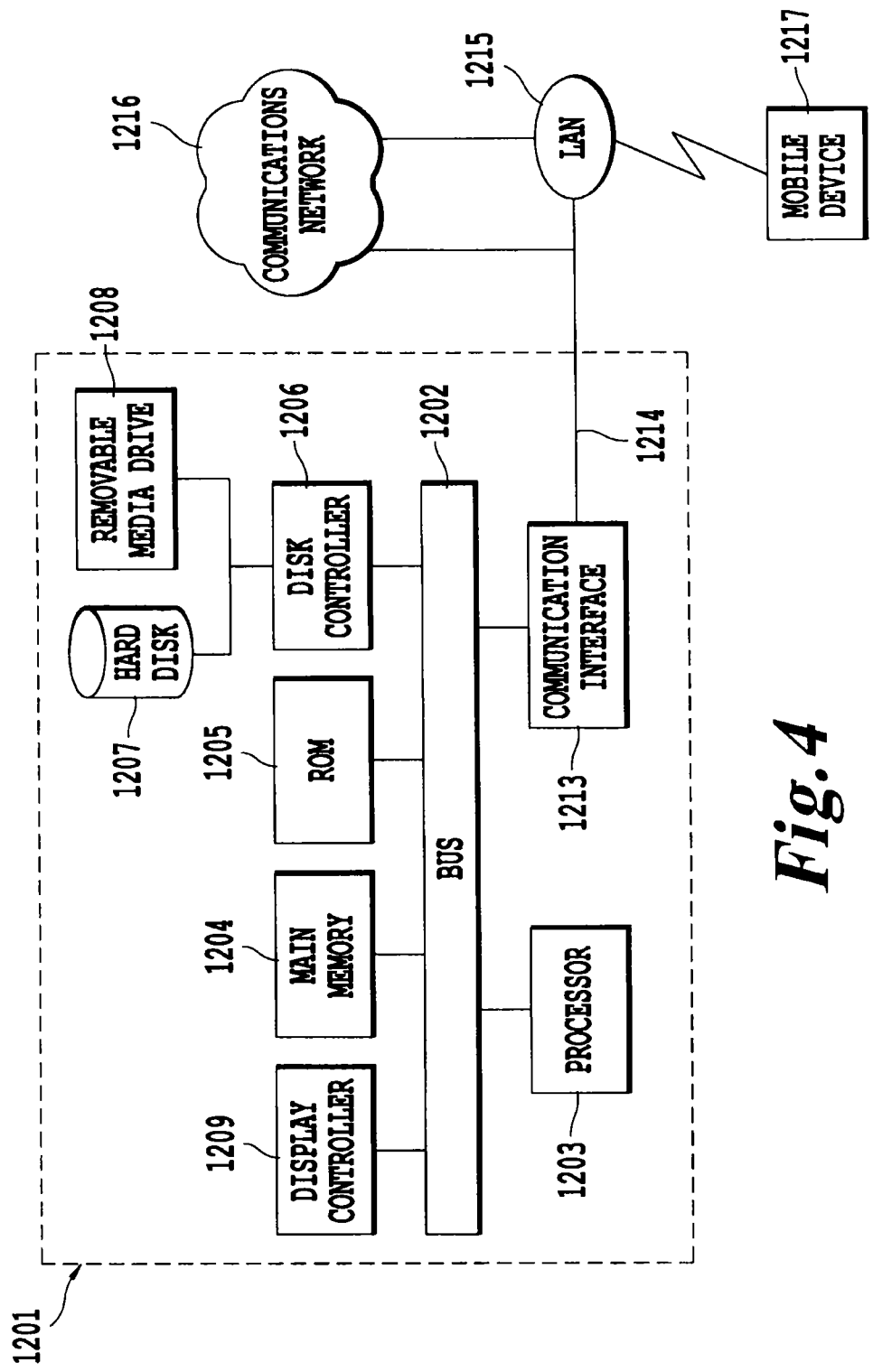
FIG. 4 illustrates an exemplary computer system for implementing various embodiments of the invention.

FIG. 4 illustrates a computer system 1201 for implementing various embodiments of the invention. The computer system 1201 may be used as the computer system 5 to perform any or all of the functions described above. The computer system 1201 includes a bus 1202 or other communication mechanism for communicating information, and a processor 1203 coupled with the bus 1202 for processing the information. The computer system 1201 also includes a main memory 1204, such as a random access memory (RAM) or other dynamic storage device (e.g., dynamic RAM (DRAM), static RAM (SRAM), and synchronous DRAM (SDRAM)), coupled to the bus 1202 for storing information and instructions to be executed by processor 1203. In addition, the main memory 1204 may be used for storing temporary variables or other intermediate information during the execution of instructions by the processor 1203. The computer system 1201 further includes a read only memory (ROM) 1205 or other static storage device (e.g., programmable read only memory (PROM), erasable PROM (EPROM), and electrically erasable PROM (EEPROM)) coupled to the bus 1202 for storing static information and instructions for the processor 1203.

The computer system 1201 also includes a disk controller 1206 coupled to the bus 1202 to control one or more storage devices for storing information and instructions, such as a magnetic hard disk 1207, and a removable media drive 1208

(e.g., floppy disk drive, read-only compact disc drive, read/write compact disc drive, compact disc jukebox, tape drive, and removable magneto-optical drive). The storage devices may be added to the computer system 1201 using an appropriate device interface (e.g., small computer system interface (SCSI), integrated device electronics (IDE), enhanced-IDE (E-IDE), direct memory access (DMA), or ultra-DMA).

The computer system 1201 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The computer system 1201 may also include a display controller 1209 coupled to the bus 1202 to control a display, such as a cathode ray tube (CRT), for displaying information to a computer user. The computer system includes input devices, such as a keyboard and a pointing device, for interacting with a computer user and providing information to the processor 1203. The pointing device, for example, may be a mouse, a trackball, or a pointing stick for communicating direction information and command selections to the processor 1203 and for controlling cursor movement on the display. In addition, a printer may provide printed listings of data stored and/or generated by the computer system 1201.

The computer system 1201 performs a portion or all of the processing steps of the invention (such as for example those described in relation to FIG. 5) in response to the processor 1203 executing one or more sequences of one or more instructions contained in a memory, such as the main memory 1204. Such instructions may be read into the main memory 1204 from another computer readable medium, such as a hard disk 1207 or a removable media drive 1208. One or more processors in a multi-processing arrangement may also be employed to execute the sequences of instructions contained in main memory 1204. In alternative embodiments, hard-wired circuitry may be used in place of or in combination with software instructions. Thus, embodiments are not limited to any specific combination of hardware circuitry and software.

As stated above, the computer system 1201 includes at least one computer readable medium or memory for holding instructions programmed according to the teachings of the invention and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes, a carrier wave (described below), or any other medium from which a computer can read.

Stored on any one or on a combination of computer readable media, the invention includes software for controlling the computer system 1201, for driving a device or devices for implementing the invention, and for enabling the computer system 1201 to interact with a human user. Such software may include, but is not limited to, device drivers, operating systems, development tools, and applications software. Such computer readable media further includes the computer program product of the invention for performing all or a portion (if processing is distributed) of the processing performed in implementing the invention.

The computer code devices of the invention may be any interpretable or executable code mechanism, including but not limited to scripts, interpretable programs, dynamic link libraries (DLLs), Java classes, and complete executable programs. Moreover, parts of the processing of the invention may be distributed for better performance, reliability, and/or cost.

The term "computer readable medium" as used herein refers to any medium that participates in providing instructions to the processor 1203 for execution. A computer readable medium may take many forms, including but not limited to, non-volatile media, volatile media, and transmission media. Non-volatile media includes, for example, optical, magnetic disks, and magneto-optical disks, such as the hard disk 1207 or the removable media drive 1208. Volatile media includes dynamic memory, such as the main memory 1204. Transmission media includes coaxial cables, copper wire and fiber optics, including the wires that make up the bus 1202. Transmission media also may also take the form of acoustic or light waves, such as those generated during radio wave and infrared data communications.

Various forms of computer readable media may be involved in carrying out one or more sequences of one or more instructions to processor 1203 for execution. For example, the instructions may initially be carried on a magnetic disk of a remote computer. The remote computer can load the instructions for implementing all or a portion of the invention remotely into a dynamic memory and send the instructions over a telephone line using a modem. A modem local to the computer system 1201 may receive the data on the telephone line and use an infrared transmitter to convert the data to an infrared signal. An infrared detector coupled to the bus 1202 can receive the data carried in the infrared signal and place the data on the bus 1202. The bus 1202 carries the data to the main memory 1204, from which the processor 1203 retrieves and executes the instructions. The instructions received by the main memory 1204 may optionally be stored on storage device 1207 or 1208 either before or after execution by processor 1203.

The computer system 1201 also includes a communication interface 1213 coupled to the bus 1202. The communication interface 1213 provides a two-way data communication coupling to a network link 1214 that is connected to, for example, a local area network (LAN) 1215, or to another communications network 1216 such as the Internet. For example, the communication interface 1213 may be a network interface card to attach to any packet switched LAN. As another example, the communication interface 1213 may be an asymmetrical digital subscriber line (ADSL) card, an integrated services digital network (ISDN) card or a modem to provide a data communication connection to a corresponding type of communications line. Wireless links may also be implemented. In any such implementation, the communication interface 1213 sends and receives electrical, electromagnetic or optical signals that carry digital data streams representing various types of information.

The network link 1214 typically provides data communication through one or more networks to other data devices. For example, the network link 1214 may provide a connection to another computer through a local network 1215 (e.g., a LAN) or through equipment operated by a service provider, which provides communication services through a communications network 1216. The local network 1214 and the communications network 1216 use, for example, electrical, electromagnetic, or optical signals that carry digital data streams, and the associated physical layer (e.g., CAT 5 cable, coaxial cable, optical fiber, etc). The signals through the various networks and the signals on the network link 1214 and through the communication interface 1213, which carry the digital data to and from the computer system 1201 maybe implemented in baseband signals, or carrier wave based signals. The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as unmodulated baseband data through a "wired" communication channel and/or sent within a predetermined frequency band, different than baseband, by modulating a carrier wave. The computer system 1201 can transmit and receive data, including program code, through the network(s) 1215 and 1216, the network link 1214, and the communication interface 1213. Moreover, the network link 1214 may provide a connection through a LAN 1215 to a mobile device 1217 such as a personal digital assistant (PDA) laptop computer, or cellular telephone.

The exemplary energy spectrum previously noted in FIG. 1 may also be used in this computer-implemented system.

The reagents and chemicals useful for methods and systems of the invention may be packaged in kits to facilitate application of the invention. In one exemplary embodiment, a kit would comprise at least one activatable agent capable of producing a predetermined cellular change, at least one energy modulation agent capable of activating the at least one activatable agent when energized, containers suitable for storing the agents in stable form, and further comprising instructions for administering the at least one activatable agent and at least one energy modulation agent to a medium, and for applying an initiation energy from an initiation energy source to activate the activatable agent. The instructions could be in any desired form, including but not limited to, printed on a kit insert, printed on one or more containers, as well as electronically stored instructions provided on an electronic storage medium, such as a computer readable storage medium. Also optionally included is a software package on a computer readable storage medium that permits the user to integrate the information and calculate a control dose, to calculate and control intensity of the irradiation source.

System Implementation

In one embodiment of the invention, there is provided a first system for producing a change in a medium disposed in an artificial container. The first system includes a mechanism configured to supply in the medium an activatable agent. The system includes an initiation energy source configured to apply an initiation energy through the artificial container to the medium to activate the at least one activatable agent in the medium.

In one embodiment, the energy modulation agent converts the applied initiation energy and produces light at an energy different from the applied initiation energy. In one embodiment, the applied initiation energy source is an external initiation energy source. In one embodiment, the applied initiation energy source is a source that is at least partially in a container holding the medium.

The medium in one embodiment is substantially transparent to the initiation energy. For example, if the medium is a liquid or fluid food product such as orange juice which has a substantial amount of suspended solids, then UV light for example as described above and even visible light will be substantially absorbed and/or scattered by the orange juice medium. Furthermore, microwave energy will likewise be absorbed by this medium. However, an initiation energy source such as an X-ray source will essentially transmit entirely through for example an orange juice medium. The effect is the medium can now be totally illuminated with the external initiation energy source.

Other sources and tuned to specific wavelengths may also be used as the initiation energy source. These sources would take advantage of an "optical window" in the medium where for example a particular wavelength of light would not be absorbed. Water selectively scatters and absorbs certain wavelengths of visible light. The long wavelengths of the light spectrum—red, yellow, and orange—can penetrate to approximately 15, 30, and 50 meters (49, 98, and 164 feet), respectively, while the short wavelengths of the light spectrum—violet, blue and green—can penetrate further. Thus, for many aqueous based systems, non-high energy X-ray sources may not be needed. In those situations, energy modulation agents would be added whose interaction with the incident light would produce for example photoactivation of catalysts in the aqueous medium.

Accordingly, depending on the medium and the energy modulation agent and the activatable agent, the initiation energy source can include at least one of an X-ray source, a gamma ray source, an electron beam source, an UV radiation source, a visible and infrared source, a microwave source, or a radio wave source. The initiation energy source can then be an energy source emitting one of electromagnetic energy, acoustic energy, or thermal energy. The initiation energy source can then be an energy source emitting a wavelength whose depth of penetration penetrates throughout the medium. The medium to be effected can be a medium to be fermented, sterilized, or cold pasteurized. The medium to be effected can include bacteria, viruses, yeasts, and fungi.

The activatable agents can be photoactivatable agents such as the photocages (described elsewhere) such that upon exposure to the initiation energy source, the photocage disassociates rendering an active agent available. The activatable agents can include agents such as psoralens, pyrene cholesteryloleate, acridine, porphyrin, fluorescein, rhodamine, 16-diazorcortisone, ethidium, transition metal complexes of bleomycin, transition metal complexes of deglycobleomycin organoplatinum complexes, alloxazines, vitamin Ks, vitamin L, vitamin metabolites, vitamin precursors, naphthoquinones, naphthalenes, naphthols and derivatives thereof having planar molecular conformations, porphorinporphyrins, dyes and phenothiazine derivatives, coumarins, quinolones, quinones, and anthroquinones. The activatable agents can include photocatalysts such as $TiO_2$, $ZnO$, $CdS$, $CdSe$, $SnO_2$, $SrTiO_3$, $WO_3$, $Fe_2O_3$, and $Ta_2O_5$ particles.

The first system can include a mechanism configured to provide in the medium at least one energy modulation agent which converts the initiation energy to an activation energy for activation of the activatable agent(s). The energy modulation agent(s) can be a photon emitter such a phosphorescent compounds, chemiluminescent compounds, and bioluminescent compounds. The energy modulation agent(s) can be up conversion or down conversion agents. The energy modulation agent(s) can be luminescent particles which emit light upon exposure to said initiation energy. The energy modulation agent(s) can be nanotubes, nanoparticles, chemilumiscent particles, and bioluminescent particles, and mixtures thereof. The luminescent particles can be chemiluminescent particles which show enhanced chemiluminescence upon exposure to microwaves.

Depending on the initiation energy source, the system can include a container for the medium that is permeable to the applied initiation energy. For example, for an X-ray source, the container can be made of aluminum, quartz, glass, or plastic. For a microwave source, the container can be made of quartz, glass, or plastic. Furthermore, the container can be a container which receives and transmits the initiation energy to fluid products to pasteurize the fluid products, or can be a container which receives and transmits the initiation energy to fluid products to remediate contaminants in the fluid products.

In another embodiment of the invention, there is provided a second system for curing a radiation-curable medium. The second system includes a mechanism configured to supply an uncured radiation-curable medium including at least one activatable agent which produces a change in the radiation-curable medium when activated, and further includes an applied initiation energy source configured to apply initiation energy to a composition including the uncured radiation-curable medium and the energy modulation agent. The energy modulation agent as described above absorbs the initiation energy and converts the initiation energy to an activation energy capable of curing the uncured medium (i.e., promoting polymerization of polymers in the uncured medium). In another example, activation of the energy modulation agent produces a light which activates the at least one photoactivatable agent to polymerize polymers in the medium.

The second system has attributes similar to the first system described above and can further permit the at least one activatable agent to include a photoinitiator such as one of benzoin, substituted benzoins, alkyl ester substituted benzoins, Michler's ketone, dialkoxyacetophenones, diethoxyacetophenone, benzophenone, substituted benzophenones, acetophenone, substituted acetophenones, xanthone, substituted xanthones, benzoin methyl ether, benzoin ethyl ether, benzoin isopropyl ether, diethoxyxanthone, chloro-thio-xanthone, azo-bisisobutyronitrile, N-methyl diethanolaminebenzophenone, camphoquinone, peroxyester initiators, non-fluorene-carboxylic acid peroxyesters and mixtures thereof.

The second system can include a container for the uncured radiation-curable medium that is permeable to the applied initiation energy. The container can be configured to contain the uncured radiation-curable medium or to hold a mold of the uncured radiation-curable medium. The container as before can be an aluminum container, a quartz container, a glass container, or a plastic container, depending on the applied initiation energy.

In one embodiment, an energy source (e.g., an external energy source) is configured to irradiate the uncured radiation-curable medium in a joint region (or regions) adhering one region of a utensil to another region of the utensil. In another embodiment, the energy source is configured to irradiate the joint regions and thereby induce sterilization of the joint regions due to the production of internal UV light inside the joint regions. In another embodiment, the energy source is configured to irradiate a surface coating.

The radiation-curable medium in the surface coating or in the mold or in other medium can include color pigments to add color to a finished cured product. The radiation-curable medium in the surface coating or in the mold or in another medium can include fumed silica to promote strength and enhance distribution of the internally generated light. The radiation-curable medium in the surface coating or in the mold or in another medium can include a moisture cure promoter to supplement the cure.

The second system provides one mechanism for production of novel radiation-cured articles, which include a radiation-cured medium and at least one energy modulation agent distributed throughout the medium. The energy modulation agent being a substance which is capable of converting an applied energy to light capable of producing a cure for the radiation-cured medium. The article can include luminescent particles such as for example nanotubes, nanoparticles, chemiluminescent particles, and bioluminescent particles, and mixtures thereof. The article can include chemiluminescent particles. The article can include color pigments or fumed silica.

In another embodiment of the invention, there is provided a third system for producing a change in a medium disposed in an artificial container. The third system includes a mechanism configured to provide to the medium 1) an activatable agent and 2) at least one energy modulation agent. The energy modulation agent converts an initiation energy to an activation energy which then activates the at least one activatable agent. The third system further includes an applied initiation energy source configured to apply the initiation energy through the artificial container to activate the at least one activatable agent in the medium.

The third system has similar attributes to the first and second systems described above, and further includes encapsulated structures including the energy modulation agent. The encapsulated structures can include nanoparticles of the energy modulation agent encapsulated with a passivation layer or can include sealed quartz or glass tubes having the energy modulation agent inside.

In another embodiment of the invention, there is provided a fourth system for producing a photo-stimulated change in a medium disposed in an artificial container. The fourth system includes a mechanism configured to provide in the medium at least one energy modulation agent. The energy modulation agent converts an initiation energy to an activation energy which then produces the photo-stimulated change. The fourth system further includes an initiation energy source configured to apply the initiation energy to the medium to activate the at least one energy modulation agent in the medium. The system can include encapsulated structures including therein the energy modulation agent. The encapsulated structures can include nanoparticles of the energy modulation agent encapsulated with a passivation layer.

The fourth system can include a container which receives and transmits the initiation energy to products within the medium. The products can include plastics, where the activation energy alters the surface structure of the plastics. The products can include polylactic acid (PLA) plastics and polyhydroxyalkanoates (PHA) plastics. In this embodiment, the activation energy can photo-graft a molecular species onto a surface of the plastics.

Sterilization Methods and System Components

Optical techniques have been often used in sterilization procedures to render unwanted or harmful waterborne microorganisms incapable of reproducing using ultraviolet light (specifically the spectral area of UV-C, 200 to 280 nm range). Ultraviolet light in the UV-C is considered the most lethal range as a germicidal disinfectant (capable of altering a living microorganism's DNA, and keeping the microorganism from reproducing). UV-C, with 264 nanometers being the peak germicidal wavelength, is known as the germicidal spectrum. Although the UV-C method is simple and effective, it is not particularly effective in samples (gas, liquids, particulates) enclosed on containers which do not transmit UV light. The present invention provides techniques and systems that can use externally applied radiation such as X-ray for sterilization. While illustrated below with respect to X-ray irradiation, and as discussed above, other suitable forms of energy could be used provided the containers and medium to be sterilized was sufficiently transparent for the medium to be thoroughly irradiated. Examples of alternative sources and materials for upconverting luminescence to higher energies have been discussed above.

These systems are applicable in a number of the applications discussed above and as well as in other sterilization areas. The systems could thus be used in the waste water detoxification, blood sterilization, cold pasteurization, and photodeactivation commercial applications discussed in the sections above. These systems (like FIGS. 3B-3D) show the use of artificial containers in which the medium to be treated is disposed.

Having generally described this invention, a further understanding can be obtained by reference to certain specific examples which are provided herein for purposes of illustration only and are not intended to be limiting unless otherwise specified.

Numerous modifications and variations of the invention are possible in light of the above teachings. It is therefore to be understood that within the scope of the appended claims, the invention may be practiced otherwise than as specifically described herein.

The invention claimed is:

1. A method for curing an adhesive, comprising:
    disposing in contact with an object an adhesive composition comprising 1) an uncured radiation-curable medium, 2) an energy modulation agent, and 3) a photoactivated photoinitiator, wherein the energy modulation agent is resistant to chemical interaction with the uncured radiation-curable medium;
    applying energy from at least one of x-rays, gamma rays, or an electron beam into the composition, wherein the energy interacts with the energy modulation agent and internally generates light inside the uncured radiation-curable medium; and
    activating the photoinitiator in the radiation-curable medium with the internally generated light and thereby curing the radiation-curable medium.

2. The method of claim 1, wherein the adhesive composition in said disposing step comprises a chemically inert energy modulation agent.

3. The method of claim 2, wherein the disposing comprises disposing a polymer coated energy modulation agent as the chemically inert energy modulation agent.

4. The method of claim 2, wherein the disposing comprises disposing a silica coated energy modulation agent as the chemically inert energy modulation agent.

5. The method of claim 2, wherein the disposing comprises disposing a zeolite-encased energy modulation agent as the chemically inert energy modulation agent.

6. The method of claim 2, wherein the disposing comprises disposing at least one of a telluride, a selenide, and an oxide semiconductor as the chemically inert energy modulation agent.

7. The method of claim 2, wherein the disposing comprises disposing at least one of $Y_2O_3$; ZnSe; Mn, Er ZnSe; Mn; Mn, Yb ZnSe; Mn, $Y_2O_3$:$Tb^{3+}$; $Y_2O_3$:$Tb^{3+}$, $Er^{3+}$; CdSe, $Y_2O_3$:$Eu^{3+}$, $Y_2O_3$:$Eu^{3+}$; BaFBr:$Tb^{3+}$; and $YF_3$:$Tb^{3+}$ as the chemically inert energy modulation agent.

8. The method of claim 1, wherein the disposing comprises disposing an adhesive composition having a concentration of $10^9$ nanoparticles/$cm^3$ of 200 nm diameter energy modulation agents.

9. The method of claim 2, wherein the disposing comprises disposing an adhesive composition having a concentration greater than $10^9$ nanoparticles/$cm^3$ of 200 diameter energy modulation agents.

10. The method of claim 1, wherein the activating comprises: activating the photoiniator with 200-280 nm wavelength ultraviolet light.

11. The method of claim 1, wherein the activating comprises: activating the photoiniator with 280-320 nm wavelength ultraviolet light.

12. The method of claim 1, wherein the activating comprises: activating the photoiniator with 320-400 nm wavelength ultraviolet light.

13. The method of claim 1, wherein the activating comprises: activating the photoiniator with 350-400 nm wavelength ultraviolet light.

14. The method of claim 1, wherein the uncured radiation-curable medium comprises a UV-curable silicone.

15. The method of claim 14, wherein the UV-curable silicone comprises an organopolysiloxane.

16. The method of claim 14, wherein the UV-curable silicone includes a methacrylate group.

17. The method of claim 14, wherein the UV-curable silicone includes an acryloxy group.

18. The method of claim 14, wherein the UV-curable silicone includes at least one of carboxylate, maleate, and cinnamate.

19. The method of claim 14, wherein the UV-curable silicone includes a free radical generator.

20. The method of claim 19, wherein the free radical generator comprises a benzoin ether.

21. The method of claim 14, wherein the UV-curable silicone includes at least one of trimethylsilyl, dimethylsilyl, phenyldimethylsilyl, vinyldimethylsilyl, trifluoropropyldimethylsilyl, (4-vinylphenyl)dimethylsilyl, (vinylbenzyl)dimethylsilyl, and (vinylphenethyl)dimethylsilyl.

22. The method of claim 1, wherein the photoinitiator comprises at least one of at least one of benzoin, substituted benzoins, alkyl ester substituted benzoins, Michler's ketone, dialkoxyacetophenones, diethoxyacetophenone, benzophenone, substituted benzophenones, acetophenone, substituted acetophenones, xanthone, substituted xanthones, benzoin methyl ether, benzoin ethyl ether, benzoin isopropyl ether, diethoxyxanthone, chloro-thio-xanthone, azo-bisisobutyronitrile, N-methyl diethanolaminebenzophenone, camphoquinone, peroxyester initiators, non-fluorene-carboxylic acid peroxyesters and mixtures thereof.

23. The method of claim 1, wherein the photoinitiator comprises a weight percentage of the uncured radiation-curable medium ranging from 0.1% to 10%.

24. The method of claim 1, wherein the photoinitiator comprises a weight percentage of the uncured radiation-curable medium ranging from 2 to 6%.

25. The method of claim 1, wherein the uncured radiation-curable medium includes a moisture cure catalyst.

26. The method of claim 22, wherein the moisture cure catalyst comprises an organic compound of at least one of titanium, tin, zirconium, and combinations thereof.

27. The method of claim 1, wherein the uncured radiation-curable medium includes an inorganic filler material.

28. The method of claim 24, wherein the inorganic filler material comprises a silica.

29. The method of claim 24, wherein the inorganic filler material comprises a color pigment.

30. The method of claim 1, wherein the uncured radiation-curable medium includes a UV curable urethane acrylate.

31. The method of claim 1, wherein the applying energy comprises: applying said energy from an external energy source of the x-rays, gamma rays, or electron beam.

32. The method of claim 1, wherein the applying energy comprises: applying 10 to 150 keV x-rays to the uncured radiation-curable medium.

33. The method of claim 1, wherein the applying energy comprises: applying said energy from a directed or focused energy source.

34. The method of claim 1, wherein the energy modulation agent comprises luminescent particles distributed throughout the uncured medium whose emission cures the uncured medium throughout the medium.

35. The method of claim 1, further comprising: filling a gap inside the object and curing the radiation-curable medium in the gap.

36. The method of claim 35, wherein the gap is inside the object.

37. The method of claim 36, wherein the object comprises at least one of a bottle cap, a prosthetic device, a concrete structure, and a storage tank.

38. The method of claim 1, wherein the disposing comprises pressure injecting said composition into said object to fill a gap inside the object.

39. The method of claim 1, wherein the curing the radiation-curable medium comprises closing a hole or a pathway in the object.

40. The method of claim 1, wherein the activating comprises adhering said first object to a second object.

41. The method of claim 40, wherein the first object comprises a medical bottle cap and the second object comprises a seal material for the medical bottle cap.

* * * * *